(12) United States Patent
Saint

(10) Patent No.: US 12,226,608 B2
(45) Date of Patent: *Feb. 18, 2025

(54) METHOD AND DEVICE UTILIZING MEDICAMENT DELIVERY PROTOCOLS

(71) Applicant: Tandem Diabetes Care, Inc., San Diego, CA (US)

(72) Inventor: Sean Saint, San Diego, CA (US)

(73) Assignee: Tandem Diabetes Care, Inc., San Diego, CA (US)

( * ) Notice: Subject to any disclaimer, the term of this patent is extended or adjusted under 35 U.S.C. 154(b) by 32 days.

This patent is subject to a terminal disclaimer.

(21) Appl. No.: 18/109,026

(22) Filed: Feb. 13, 2023

(65) Prior Publication Data

US 2023/0277761 A1 Sep. 7, 2023

Related U.S. Application Data

(63) Continuation of application No. 16/664,177, filed on Oct. 25, 2019, now Pat. No. 11,596,731, which is a (Continued)

(51) Int. Cl.
*A61M 5/142* (2006.01)
*A61M 5/152* (2006.01)
(Continued)

(52) U.S. Cl.
CPC ........ *A61M 5/14244* (2013.01); *A61M 5/152* (2013.01); *A61M 2005/14208* (2013.01);
(Continued)

(58) Field of Classification Search
CPC .............. A61M 5/14244; A61M 5/152; A61M 2005/14208; A61M 2005/14268; G16H 20/17; G16H 40/67
See application file for complete search history.

(56) References Cited

U.S. PATENT DOCUMENTS 2,462,596 A 2/1949 Bent
2,629,376 A 2/1953 Pierre et al.
(Continued)

FOREIGN PATENT DOCUMENTS

DE 399065 C 7/1924
DE 19819407 A1 11/1999
(Continued)

OTHER PUBLICATIONS

Application and File History for U.S. Appl. No. 15/340,339, filed Nov. 1, 2016, inventor Saint.

*Primary Examiner* — Theodore J Stigell
(74) *Attorney, Agent, or Firm* — Merchant & Gould P.C.

(57) ABSTRACT

A method of infusing liquid medicaments including insulin via an insulin pump, includes identifying an insulin delivery protocol associated with ingestion of carbohydrates wherein the insulin delivery protocol is likely to lead to a postprandial drop in blood glucose to a level below a basal level, then proposing at least one alternative insulin delivery protocol to inhibit the postprandial drop in blood glucose by delivering a metered amount of insulin that is appropriate to facilitate the metabolism of the carbohydrates without the postprandial blood glucose level drop. The invention further includes querying the patient as to whether to apply the alternative insulin delivery protocol, receiving instructions from the patient in response to the query, and applying the alternative insulin delivery protocol following receiving instructions from the patient to apply the alternative insulin delivery protocol.

16 Claims, 20 Drawing Sheets

Related U.S. Application Data continuation of application No. 15/340,339, filed on Nov. 1, 2016, now Pat. No. 10,463,786, which is a continuation of application No. 13/841,432, filed on Mar. 15, 2013, now Pat. No. 9,492,608.

(51) Int. Cl.
  *G16H 20/17* (2018.01)
  *G16H 40/67* (2018.01)

(52) U.S. Cl.
  CPC ... *A61M 2005/14268* (2013.01); *G16H 20/17* (2018.01); *G16H 40/67* (2018.01)

(56) References Cited

U.S. PATENT DOCUMENTS

| | | | |
|---|---|---|---|
| 2,691,542 A | 10/1954 | Chenoweth | |
| 3,059,639 A | 10/1962 | Blackman et al. | |
| 4,810,243 A | 3/1989 | Howson | |
| 5,395,326 A | 3/1995 | Haber et al. | |
| 5,431,627 A | 7/1995 | Pastrone et al. | |
| 5,685,844 A | 11/1997 | Marttila | |
| 5,788,669 A | 8/1998 | Peterson | |
| 5,800,420 A | 9/1998 | Gross et al. | |
| 5,807,375 A | 9/1998 | Gross et al. | |
| 5,820,622 A | 10/1998 | Gross et al. | |
| 5,860,957 A | 1/1999 | Jacobsen et al. | |
| 5,919,216 A | 7/1999 | Houben et al. | |
| 5,935,598 A | 8/1999 | Sage et al. | |
| 5,961,483 A | 10/1999 | Sage et al. | |
| 6,034,054 A | 3/2000 | Defelippis et al. | |
| 6,165,155 A | 12/2000 | Jacobsen et al. | |
| 6,175,752 B1 | 1/2001 | Say et al. | |
| 6,306,420 B1 | 10/2001 | Cheikh | |
| 6,471,689 B1 | 10/2002 | Joseph et al. | |
| 6,485,461 B1 | 11/2002 | Mason et al. | |
| 6,520,936 B1 | 2/2003 | Mann | |
| 6,544,212 B2 | 4/2003 | Galley et al. | |
| 6,544,229 B1 | 4/2003 | Danby et al. | |
| 6,551,992 B1 | 4/2003 | Defelippis et al. | |
| 6,558,351 B1 | 5/2003 | Steil et al. | |
| 6,565,509 B1 | 5/2003 | Say et al. | |
| 6,572,542 B1 | 6/2003 | Houben et al. | |
| 6,589,229 B1 | 7/2003 | Connelly et al. | |
| 6,649,403 B1 | 11/2003 | McDevitt et al. | |
| 6,702,779 B2 | 3/2004 | Connelly et al. | |
| 6,740,072 B2 | 5/2004 | Starkweather et al. | |
| 6,744,350 B2 | 6/2004 | Blomquist | |
| 6,759,386 B2 | 7/2004 | Franco | |
| 6,827,702 B2 | 12/2004 | Lebel et al. | |
| 6,835,194 B2 | 12/2004 | Johnson et al. | |
| 6,852,104 B2 | 2/2005 | Blomquist | |
| 6,862,466 B2 | 3/2005 | Ackerman | |
| 6,906,028 B2 | 6/2005 | Defelippis et al. | |
| 6,949,081 B1 | 9/2005 | Chance | |
| 6,973,374 B2 | 12/2005 | Ader | |
| 6,998,387 B1 | 2/2006 | Goke et al. | |
| 6,999,854 B2 | 2/2006 | Roth | |
| 7,008,413 B2 | 3/2006 | Kovach et al. | |
| 7,072,725 B2 | 7/2006 | Bristol | |
| 7,091,179 B2 | 8/2006 | Franco | |
| 7,153,823 B2 | 12/2006 | Franco | |
| 7,166,280 B2 | 1/2007 | Franco | |
| 7,256,888 B2 | 8/2007 | Staehr et al. | |
| 7,258,864 B2 | 8/2007 | Clark | |
| 7,267,665 B2 | 9/2007 | Steil et al. | |
| 7,316,899 B2 | 1/2008 | McDevitt et al. | |
| 7,354,420 B2 | 4/2008 | Steil et al. | |
| 7,384,410 B2 | 6/2008 | Eggers et al. | |
| 7,402,153 B2 | 7/2008 | Steil et al. | |
| 7,407,490 B2 | 8/2008 | Bendsen et al. | |
| 7,514,401 B2 | 4/2009 | Franco | |
| 7,515,060 B2 | 4/2009 | Blomquist | |
| 7,517,530 B2 | 4/2009 | Clark | |
| 7,569,030 B2 | 8/2009 | Lebel et al. | |
| 7,572,789 B2 | 8/2009 | Cowen et al. | |
| 7,594,889 B2 | 9/2009 | St. Ores et al. | |
| 7,642,232 B2 | 1/2010 | Green et al. | |
| 7,674,485 B2 | 3/2010 | Bhaskaran et al. | |
| 7,678,762 B2 | 3/2010 | Green et al. | |
| 7,678,763 B2 | 3/2010 | Green et al. | |
| 7,734,323 B2 | 6/2010 | Blomquist et al. | |
| 7,736,344 B2 | 6/2010 | Moberg et al. | |
| 7,744,589 B2 | 6/2010 | Mounce et al. | |
| 7,751,907 B2 | 7/2010 | Blomquist | |
| 7,751,908 B2 | 7/2010 | Chang et al. | |
| 7,766,831 B2 | 8/2010 | Essenpreis et al. | |
| 7,771,385 B2 | 8/2010 | Eggers et al. | |
| 7,771,386 B2 | 8/2010 | Eggers et al. | |
| 7,780,981 B2 | 8/2010 | Dipierro et al. | |
| 7,785,313 B2 | 8/2010 | Mastrototaro | |
| 7,806,886 B2 | 10/2010 | Kanderian, Jr. et al. | |
| 7,811,279 B2 | 10/2010 | John | |
| 7,850,641 B2 | 12/2010 | Lebel et al. | |
| 7,860,544 B2 | 12/2010 | Say et al. | |
| 7,860,583 B2 | 12/2010 | Condurso et al. | |
| 7,869,853 B1 | 1/2011 | Say et al. | |
| 7,885,699 B2 | 2/2011 | Say et al. | |
| 7,905,868 B2 | 3/2011 | Moberg et al. | |
| 7,920,907 B2 | 4/2011 | McGarraugh et al. | |
| 7,941,200 B2 | 5/2011 | Weinert et al. | |
| 7,963,946 B2 | 6/2011 | Moubayed et al. | |
| 7,963,954 B2 | 6/2011 | Kavazov | |
| 7,972,296 B2 | 7/2011 | Braig et al. | |
| 7,976,870 B2 | 7/2011 | Berner et al. | |
| 8,025,634 B1 | 9/2011 | Moubayed et al. | |
| 8,062,249 B2 | 11/2011 | Wilinska et al. | |
| 8,070,742 B2 | 12/2011 | Woo | |
| 8,088,098 B2 | 1/2012 | Yodfat et al. | |
| 8,105,268 B2 | 1/2012 | Lebel et al. | |
| 8,118,782 B2 | 2/2012 | Remde | |
| 8,119,593 B2 | 2/2012 | Richardson et al. | |
| 8,121,857 B2 | 2/2012 | Galasso et al. | |
| 8,149,131 B2 | 4/2012 | Blomquist | |
| 8,152,789 B2 | 4/2012 | Starkweather et al. | |
| 8,177,716 B2 | 5/2012 | Say et al. | |
| 8,182,445 B2 | 5/2012 | Moubayed et al. | |
| 8,182,461 B2 | 5/2012 | Pope et al. | |
| 8,187,228 B2 | 5/2012 | Bikovsky | |
| 8,208,984 B2 | 6/2012 | Blomquist et al. | |
| 8,219,222 B2 | 7/2012 | Blomquist | |
| 8,221,345 B2 | 7/2012 | Blomquist | |
| 8,226,558 B2 | 7/2012 | Say et al. | |
| 8,235,938 B2 | 8/2012 | Eggers et al. | |
| 8,250,483 B2 | 8/2012 | Blomquist | |
| 8,257,300 B2 | 9/2012 | Budiman et al. | |
| 8,275,438 B2 | 9/2012 | Simpson | |
| 8,285,328 B2 | 10/2012 | Caffey et al. | |
| 8,287,454 B2 | 10/2012 | Wolpert et al. | |
| 8,287,495 B2 | 10/2012 | Michaud et al. | |
| 8,298,184 B2 | 10/2012 | Diperna et al. | |
| 8,333,752 B2 | 12/2012 | Veit et al. | |
| 8,337,469 B2 | 12/2012 | Eberhart et al. | |
| 8,340,792 B2 | 12/2012 | Condurso et al. | |
| 8,346,399 B2 | 1/2013 | Blomquist | |
| 8,348,886 B2 | 1/2013 | Kanderian, Jr. et al. | |
| 8,348,923 B2 | 1/2013 | Kanderian, Jr. et al. | |
| 8,357,091 B2 | 1/2013 | Say et al. | |
| 8,377,031 B2 | 2/2013 | Hayter et al. | |
| 8,380,273 B2 | 2/2013 | Say et al. | |
| 8,385,972 B2 | 2/2013 | Bochenko et al. | |
| 8,398,592 B2 | 3/2013 | Leibner-Druska | |
| 8,409,131 B2 | 4/2013 | Say et al. | |
| 8,435,206 B2 | 5/2013 | Evans et al. | |
| 8,449,524 B2 | 5/2013 | Braig et al. | |
| 8,454,576 B2 | 6/2013 | Mastrototaro et al. | |
| 8,465,460 B2 | 6/2013 | Yodfat et al. | |
| 8,512,276 B2 | 8/2013 | Talbot et al. | |
| 8,562,558 B2 | 10/2013 | Kamrath et al. | |
| 8,568,357 B2 | 10/2013 | Ortega et al. | |
| 8,657,779 B2 | 2/2014 | Blomquist | |
| 8,753,316 B2 | 6/2014 | Blomquist | |
| 8,882,701 B2 | 11/2014 | Debelser et al. | |
| 8,926,561 B2 | 1/2015 | Verhoef | |

(56) References Cited

U.S. PATENT DOCUMENTS

| | | |
|---|---|---|
| 8,952,794 B2 | 2/2015 | Blomquist |
| 9,364,679 B2 | 6/2016 | John |
| 9,474,856 B2 | 10/2016 | Blomquist |
| 9,492,608 B2 * | 11/2016 | Saint ................ A61M 5/14244 |
| 9,603,995 B2 | 3/2017 | Rosinko et al. |
| 9,737,656 B2 | 8/2017 | Rosinko |
| 9,940,441 B2 | 4/2018 | Walsh |
| 10,016,561 B2 | 7/2018 | Saint et al. |
| 10,049,768 B2 | 8/2018 | Blomquist |
| 10,201,656 B2 | 2/2019 | Rosinko |
| 10,279,105 B2 | 5/2019 | Rosinko |
| 10,357,607 B2 | 7/2019 | Blomquist et al. |
| 10,463,786 B2 * | 11/2019 | Saint ..................... A61M 5/152 |
| 11,596,731 B2 * | 3/2023 | Saint ..................... A61M 5/152 |
| 2002/0143580 A1 | 10/2002 | Bristol |
| 2002/0169636 A1 | 11/2002 | Eggers |
| 2003/0036683 A1 | 2/2003 | Kehr |
| 2003/0145854 A1 | 8/2003 | Hickle |
| 2003/0161744 A1 | 8/2003 | Vilks et al. |
| 2003/0163088 A1 | 8/2003 | Blomquist |
| 2003/0163789 A1 | 8/2003 | Blomquist |
| 2004/0068230 A1 | 4/2004 | Estes et al. |
| 2004/0176984 A1 | 9/2004 | White |
| 2005/0065464 A1 | 3/2005 | Talbot et al. |
| 2005/0096593 A1 | 5/2005 | Pope et al. |
| 2005/0143864 A1 | 6/2005 | Blomquist |
| 2005/0177395 A1 | 8/2005 | Blomquist |
| 2005/0182358 A1 | 8/2005 | Veit |
| 2005/0238507 A1 | 10/2005 | Diianni et al. |
| 2005/0277912 A1 | 12/2005 | John |
| 2006/0093785 A1 | 5/2006 | Hickle |
| 2007/0299389 A1 | 12/2007 | Halbert |
| 2008/0004601 A1 | 1/2008 | Jennewine et al. |
| 2008/0033360 A1 | 2/2008 | Evans et al. |
| 2008/0033361 A1 | 2/2008 | Evans et al. |
| 2008/0033402 A1 | 2/2008 | Blomquist |
| 2008/0033749 A1 | 2/2008 | Blomquist |
| 2008/0034323 A1 | 2/2008 | Blomquist |
| 2008/0051711 A1 | 2/2008 | Mounce et al. |
| 2008/0051716 A1 | 2/2008 | Stutz |
| 2008/0058773 A1 | 3/2008 | John |
| 2008/0071210 A1 | 3/2008 | Moubayed |
| 2008/0097289 A1 | 4/2008 | Steil et al. |
| 2008/0097291 A1 | 4/2008 | Hanson et al. |
| 2008/0097375 A1 | 4/2008 | Bikovsky |
| 2008/0126969 A1 | 5/2008 | Blomquist |
| 2008/0171967 A1 * | 7/2008 | Blomquist ............. G16H 70/00 604/67 |
| 2008/0172026 A1 | 7/2008 | Blomquist |
| 2008/0172027 A1 | 7/2008 | Blomquist |
| 2008/0172028 A1 | 7/2008 | Blomquist |
| 2008/0172029 A1 | 7/2008 | Blomquist |
| 2008/0172030 A1 | 7/2008 | Blomquist |
| 2008/0172031 A1 | 7/2008 | Blomquist |
| 2008/0177165 A1 | 7/2008 | Blomquist et al. |
| 2008/0183060 A1 | 7/2008 | Steil et al. |
| 2008/0228056 A1 | 9/2008 | Blomquist et al. |
| 2008/0269714 A1 | 10/2008 | Mastrototaro et al. |
| 2008/0269723 A1 | 10/2008 | Mastrototaro et al. |
| 2008/0281297 A1 | 11/2008 | Pesach |
| 2008/0306434 A1 | 12/2008 | Dobbles et al. |
| 2008/0306444 A1 | 12/2008 | Brister et al. |
| 2009/0036870 A1 | 2/2009 | Mounce et al. |
| 2009/0043290 A1 | 2/2009 | Villegas et al. |
| 2009/0062729 A1 | 3/2009 | Woo |
| 2009/0118592 A1 | 5/2009 | Klitgaard |
| 2009/0137987 A1 | 5/2009 | Ali |
| 2009/0171324 A1 | 7/2009 | Chong et al. |
| 2009/0247982 A1 | 10/2009 | Krulevitch et al. |
| 2009/0259183 A1 | 10/2009 | Chong et al. |
| 2009/0259198 A1 | 10/2009 | Chong et al. |
| 2009/0259209 A1 | 10/2009 | Chong et al. |
| 2009/0270810 A1 | 10/2009 | Debelser et al. |
| 2009/0270811 A1 | 10/2009 | Mounce et al. |
| 2009/0270833 A1 | 10/2009 | Debelser et al. |
| 2009/0326458 A1 | 12/2009 | Chong et al. |
| 2010/0016791 A1 | 1/2010 | Chong et al. |
| 2010/0081993 A1 | 4/2010 | O'Connor |
| 2010/0094110 A1 | 4/2010 | Heller |
| 2010/0114015 A1 | 5/2010 | Kanderian, Jr. et al. |
| 2010/0121170 A1 | 5/2010 | Rule |
| 2010/0125241 A1 | 5/2010 | Prud et al. |
| 2010/0145262 A1 | 6/2010 | Bengtsson et al. |
| 2010/0145303 A1 * | 6/2010 | Yodfat .............. A61M 5/14244 604/151 |
| 2010/0152644 A1 | 6/2010 | Pesach |
| 2010/0198143 A1 | 8/2010 | Estes et al. |
| 2010/0198520 A1 | 8/2010 | Breton et al. |
| 2010/0218132 A1 | 8/2010 | Soni et al. |
| 2010/0234709 A1 | 9/2010 | Say et al. |
| 2010/0249561 A1 | 9/2010 | Patek et al. |
| 2010/0262117 A1 | 10/2010 | Magni et al. |
| 2010/0262434 A1 | 10/2010 | Shaya |
| 2010/0286467 A1 | 11/2010 | Pesach |
| 2010/0286653 A1 | 11/2010 | Kubel et al. |
| 2010/0292634 A1 | 11/2010 | Kircher, Jr. et al. |
| 2010/0298681 A1 | 11/2010 | Say et al. |
| 2010/0305545 A1 | 12/2010 | Kanderian, Jr. et al. |
| 2010/0324382 A1 | 12/2010 | Cantwell et al. |
| 2011/0009823 A1 | 1/2011 | Chong et al. |
| 2011/0009825 A1 | 1/2011 | Chong et al. |
| 2011/0030845 A1 | 2/2011 | Chong et al. |
| 2011/0054391 A1 | 3/2011 | Ward et al. |
| 2011/0071464 A1 | 3/2011 | Palerm |
| 2011/0071765 A1 | 3/2011 | Yodfat et al. |
| 2011/0077481 A1 | 3/2011 | Say et al. |
| 2011/0092788 A1 | 4/2011 | Long et al. |
| 2011/0098548 A1 | 4/2011 | Budiman et al. |
| 2011/0106011 A1 | 5/2011 | Cinar et al. |
| 2011/0112505 A1 | 5/2011 | Starkweather et al. |
| 2011/0112506 A1 | 5/2011 | Starkweather et al. |
| 2011/0118578 A1 | 5/2011 | Timmerman |
| 2011/0124996 A1 | 5/2011 | Reinke et al. |
| 2011/0144586 A1 | 6/2011 | Michaud et al. |
| 2011/0144616 A1 | 6/2011 | Michaud et al. |
| 2011/0152770 A1 | 6/2011 | Diperna et al. |
| 2011/0152824 A1 | 6/2011 | Diperna et al. |
| 2011/0160650 A1 | 6/2011 | Chong et al. |
| 2011/0160654 A1 | 6/2011 | Hanson et al. |
| 2011/0160666 A1 | 6/2011 | Hanson et al. |
| 2011/0160678 A1 | 6/2011 | Chong et al. |
| 2011/0166544 A1 | 7/2011 | Verhoef et al. |
| 2011/0178461 A1 | 7/2011 | Chong et al. |
| 2011/0190700 A1 | 8/2011 | Kavazov et al. |
| 2011/0192478 A1 | 8/2011 | Chong et al. |
| 2011/0196213 A1 | 8/2011 | Thukral et al. |
| 2011/0213306 A1 | 9/2011 | Hanson et al. |
| 2011/0275410 A1 | 11/2011 | Caffey |
| 2012/0004637 A1 | 1/2012 | Krulevitch et al. |
| 2012/0029433 A1 | 2/2012 | Michaud et al. |
| 2012/0029468 A1 | 2/2012 | Diperna |
| 2012/0030610 A1 | 2/2012 | Diperna et al. |
| 2012/0232484 A1 | 9/2012 | Blomquist |
| 2012/0232521 A1 | 9/2012 | Blomquist |
| 2012/0265722 A1 | 10/2012 | Blomquist |
| 2012/0330227 A1 | 12/2012 | Budiman et al. |
| 2013/0015980 A1 | 1/2013 | Evans |
| 2013/0046281 A1 | 2/2013 | Javitt |
| 2013/0191770 A1 | 7/2013 | Bartz |
| 2013/0237947 A1 | 9/2013 | Amirouche |
| 2013/0324824 A1 | 12/2013 | Kamath |
| 2014/0005633 A1 | 1/2014 | Finan |
| 2014/0163919 A1 | 6/2014 | Manigel |
| 2014/0276420 A1 | 9/2014 | Rosinko |
| 2014/0276531 A1 | 9/2014 | Walsh |
| 2014/0276556 A1 | 9/2014 | Saint et al. |
| 2014/0276574 A1 | 9/2014 | Saint |
| 2014/0351712 A1 | 11/2014 | Blomquist |
| 2015/0182693 A1 | 7/2015 | Rosinko |
| 2015/0182695 A1 | 7/2015 | Rosinko |
| 2015/0314062 A1 | 11/2015 | Blomquist et al. |
| 2015/0352282 A1 | 12/2015 | Mazlish |
| 2016/0082188 A1 | 3/2016 | Blomquist et al. |
| 2016/0228041 A1 | 8/2016 | Heller |

(56) References Cited

U.S. PATENT DOCUMENTS

| | | |
|---|---|---|
| 2017/0056590 A1 | 3/2017 | Diperna et al. |
| 2018/0021514 A1 | 1/2018 | Rosinko |
| 2018/0133396 A1 | 5/2018 | McLaughlin |

FOREIGN PATENT DOCUMENTS

| | | |
|---|---|---|
| EP | 2410448 A2 | 1/2012 |
| WO | WO-03082091 A2 | 10/2003 |
| WO | WO-2006127841 A2 | 11/2006 |
| WO | WO-2007065944 A1 | 6/2007 |
| WO | WO-2008127694 A1 | 10/2008 |
| WO | WO-2009016636 A2 | 2/2009 |
| WO | WO-2009124133 A2 | 10/2009 |
| WO | WO-2011014704 A2 | 2/2011 |
| WO | WO-2018089787 A1 | 5/2018 |

* cited by examiner

METHOD AND DEVICE UTILIZING MEDICAMENT DELIVERY PROTOCOLS

RELATED APPLICATIONS

This application is a continuation of application Ser. No. 16/664,177, filed Oct. 25, 2019, which is a continuation of application Ser. No. 15/340,339 filed Nov. 1, 2016, which is a continuation of application Ser. No. 13/841,432 filed Mar. 15, 2013, now U.S. Pat. No. 9,492,608 issued Nov. 15, 2016, which is hereby fully incorporated herein by reference.

FIELD OF THE INVENTION

The invention relates generally to insulin pumps that are utilized for controlled infusion of insulin into the human body. Insulin pumps may also include dual hormone therapy devices that infuse insulin and another hormone or medication into the body. More particularly, the invention relates to profiles that are used to control the infusion of insulin and other medicaments in the treatment of diabetes.

BACKGROUND OF THE INVENTION

There are many applications in academic, industrial, and medical fields, as well as others, that may benefit from devices and methods that are capable of accurately and controllably delivering fluids, including liquids and gases that have a beneficial effect when administered in known and controlled quantities. Such devices and methods may be particularly useful in the medical field where much of the treatments for a large percentage of patients includes the administration of a known amount of a substance at predetermined intervals.

Insulin-injecting pumps have been developed for the administration of insulin for those suffering from both type I and II diabetes. Recently continuous subcutaneous insulin injection and/or infusion therapy has been adapted for the treatment of diabetes. Such therapy may include the regular and/or continuous injection or infusion of insulin into or under the skin of a person suffering from diabetes and offers an alternative to multiple daily injections of insulin by an insulin syringe or an insulin pen.

Generally, present insulin pump therapy is based on the use and application of currently available, so-called, "rapid-acting" insulin analogues, including insulin lispro (marketed by Eli Lily & Company under the trademark Humalog®), insulin glulisine (marketed by Sanofi-Aventis under the trademark Apidra®), and insulin aspart (marketed by Novo Nordisk under the trademark NovoLog®). More recently, ultra-rapid acting insulins have been developed. Further, other drugs have been developed that either modify insulin action time or alter the rate of metabolism of food. These all change the way that post-prandial blood glucose levels behave in a somewhat similar fashion.

Currently, in presently available insulin pumps, an insulin bolus is delivered as rapidly as it can be. The delivery of an insulin bolus creates an abrupt rise in the level of insulin in the blood stream which encourages the rapid metabolism of glucose. The beginning of insulin appearance in the blood stream is delayed from the time of infusion because of the time required for insulin absorption and distribution in the circulation. With ultra-rapid acting insulins the delay time is less than for fast acting insulin. Thus, the delivery of such an insulin bolus according to a "normal" protocol may cause an excessive metabolism of glucose thereby causing a drop in blood glucose which can be dangerous. In extreme cases, the drop in blood glucose can lead to insulin shock, which is also known as hypoglycemic shock. In rare cases hypoglycemic shock can even cause death.

The use of pramlintide, (e.g., pramlintide acetate marketed by Bristol Myers-Squibb under the trademark Symlin®) is becoming increasingly common in the treatment of type I diabetes. Pramlintide is synthetic amylin, an agent that acts to slow the rate of gastric emptying and therefore the rate at which food is released into the small intestine. Accordingly, this slows the rate at which food is metabolized. Glucagon-like peptide-1 (GLP-1) agonist therapy may also be used to slow the rate of gastric emptying which in turn slows the rate of absorption of food in the small intestine. The use of these agents results in a less pronounced rise in blood sugar after eating that also may last for a longer period of time.

The development of new insulins as well as adjunctive medicinal therapy for diabetes creates a need for new therapy protocols to be used with an insulin pump or a dual therapy insulin pump.

SUMMARY OF THE INVENTION

The present invention solves many of the above-indicated problems and assists individuals under treatment for diabetes in attaining the goal of as constant a blood sugar level as possible. The maintenance of a constant blood sugar level is expected to reduce the damaging sequelae of diabetes mellitus that include microvascular changes in the eyes and elsewhere in the body such as retinopathy, nephropathy and neuropathy as well cardiovascular disease.

According to the invention, current insulin pump based therapies in which a bolus of insulin is delivered as quickly as it can be, thus creating a rapid rise in insulin level, are modified to accommodate more rapidly acting insulins and complementary drug therapies, such as pramlintide, which cause a similar post-prandial effect by slowing the rate at which food is emptied from the stomach and thus the metabolism of carbohydrates. The invention is also useful with modified insulin that has insulin action time modifiers, such as hyaluronidase, added to it. Further, the invention also is well suited to be used along with insulin infusion site modifiers. For example, this includes but is not limited to, products that apply heat to the infusion site. If the insulin infusion site is heated, the absorption of insulin is facilitated. Other insulin infusion site modifiers are being developed as well.

In one embodiment, the invention includes a method of providing dual hormone therapy for diabetes in which two hormones are supplied from separate compartments in the same insulin pump and a controller is utilized to maintain a memory when pramlintide (or another agent that slows gastric emptying) has been administered and when it has not. Accordingly, based on this information, the pump can be activated to provide a standard insulin bolus or to provide an extended or other new type of insulin bolus as discussed herein. The extent to which a bolus is extended is governed by a new metric not currently used in prior art insulin pumps.

According to one embodiment of the invention, a ratio comparing minutes of bolus extension to the dose of pramlintide (or other agent) is used. Accordingly, if a sufficiently large amount of carbohydrate is ingested above a predetermined threshold, a dose of pramlintide (or other agent) may be given. In this case, a bolus of insulin may be infused along with an insulin bolus extension. According to an embodiment of the invention, the length of the extension is proportional to the dose of pramlintide. According to another embodiment of the invention, an extended bolus may be given if a dose of pramlintide exceeds a certain predetermined threshold.

According to another embodiment of the invention, a bolus whose shape can be represented in a graph is more similar to a single sine wave or a Gaussian distribution to approximate the expected post-prandial rise in blood glucose levels. Current insulin pumps deliver boluses that are either abrupt and immediate or where a fraction of the bolus is delivered immediately and a remaining fraction is delivered over an extended period of time. As the speed of insulin action increases it is desirable for the shape of the insulin infusion profile to more closely match the shape of the carbohydrate profile.

According to another embodiment of the invention, a small amount of insulin is delivered in a first dose followed by an increased second amount of insulin delivered following a period of time, again followed by a third decreased amount of insulin delivered.

According to another embodiment of the invention, metrics that are used are the time to peak bolus and the total bolus extension of time. According to the invention, these two metrics are used to govern the shape of a sine wave like bolus. The goal of therapy under the present invention is to provide the required amount of insulin at the right time relative to blood sugar control so that the blood sugar level may be maintained at a constant level as possible. Slower food movement into the small intestine as controlled by pramlintide and related medications and the utilization of ultra-rapid acting insulins, as controlled by the invention, may permit better overall blood sugar control than has previously been possible.

The goal of the invention is to match the rate at which food is metabolized to the rate at which insulin becomes active. A concern with ultra-rapid acting insulins is that the insulin may act faster than the food uptake that causes a rise in blood sugar. Accordingly, there even may be a postprandial drop in blood glucose level rather than the normally expected rise. According to the invention, with the use of ultra-rapid acting insulins, meal boluses are carbohydrates boluses that may be extended. According to one embodiment of the invention, the shape of the extension is similar to a sine wave or Gaussian curve.

According to the invention, with both pramlintide (or other like acting medicaments) use and ultra-rapid acting insulin use, it is likely that a correction bolus should be infused immediately. If the patient using the pump promptly enters meal boluses or carbohydrate boluses, the controller of the insulin pump can track delivery of a correction or a meal bolus and a particular bolus shape can be suggested to the patient.

According to the invention, even combination boluses where a part of the bolus is for correction and part of the boluses is intended to accommodate a future meal are calculated and delivered.

Another context in which the invention is applicable is in therapy where insulin action time modifiers are included as an adjunct to standard insulin therapy. For example, it is known that the inclusion of hyaluronidase to insulin causes the standard insulin to act more rapidly. According to the invention, with the use of insulin action time modifiers, either mixed directly with the insulin within the same injection or separately injected using a dual drug insulin pump. Insulin boluses are modified or extended as described herein.

According to one embodiment of the invention, the amount of extension is based on a ratio of insulin to the modifier that is injected. Thus, the invention also includes an additional metric that is used to calculate the proper insulin dose.

According to embodiments of the invention, the metric is based on a ratio of insulin to modifier or may be based on a number of minutes of bolus extension of insulin per dose of modifier. Thus the period of extension is proportional to the dose of modifier. According to another embodiment of the invention, a combination of the ratio of insulin to modifier and a period of extension per dose of modifier is used. Further, an alternative insulin delivery protocol may be appropriate if hyalouronidase or another insulin action modifier has been given over some predetermined earlier time span. For example, if the modifier has been used by the patient in the last 24 or 48 hours it may be appropriate to use an alternative insulin delivery protocol as described herein.

Further, if the dual drug pump is utilized, the pump controller can track when both drugs are pumped and therefore predict when to apply the correction.

Further, according to another embodiment of the invention, if insulin and the modifier are mixed, the mixing ratio is entered into the pump controller so that the pump can calculate how much to extend or modify boluses.

Rapid changes in blood glucose level can cause patients with diabetes to feel uncomfortable or emotionally out of balance in ways that patients find hard to describe. This can occur when an excessively large insulin bolus is delivered or if the patient engages in exercise with an excess of insulin in his system. With increasing speed of insulin action it may be desirable to extend even correction boluses to reduce the rate of change of blood sugar level. Thus, according to another embodiment, the invention includes an alternative insulin delivery protocol wherein a correction bolus is delivered that includes a correction bolus extension to moderate the rate at which blood glucose change occurs. According to another embodiment, the invention includes utilizing an alternative insulin delivery protocol that maintains the rate of change of blood glucose below a preselected level.

DETAILED DESCRIPTION

The invention generally applies to the operation and utilization of insulin infusion pumps. Included below is a description of an insulin infusion pump with which the methods of the invention may be used.

Provided herein are systems, devices and methods for identifying an insulin delivery protocol associated with ingestion of carbohydrates wherein the insulin delivery protocol is likely to lead to a postprandial drop in blood glucose to a level below a basal level that is likely to deprive a patient of sufficient blood glucose to function normally. The invention also includes proposing at least one alternative insulin delivery protocol to inhibit the postprandial drop in blood glucose by delivering a metered amount of insulin that is appropriate to facilitate the metabolism of the carbohydrates without the postprandial blood glucose drop. The inventions are usable in the context of an infusion pump and particularly in an insulin pump. Some embodiments may include advances in the internal components, the control circuitry, and improvements in a user interface of the systems and devices. The advances may allow for a safer and more accurate delivery of medicament to a patient than is currently attainable today from other devices, systems, and methods. Although embodiments described herein may be discussed in the context of the controlled delivery of insulin, delivery of other medicaments as well as other applications are also contemplated. Device and method embodiments discussed herein may be used for pain medication, chemotherapy, iron chelation, immunoglobulin treatment, dextrose or saline IV delivery, or any other suitable indication or application. Non-medical applications are also contemplated.

Figure 1A:
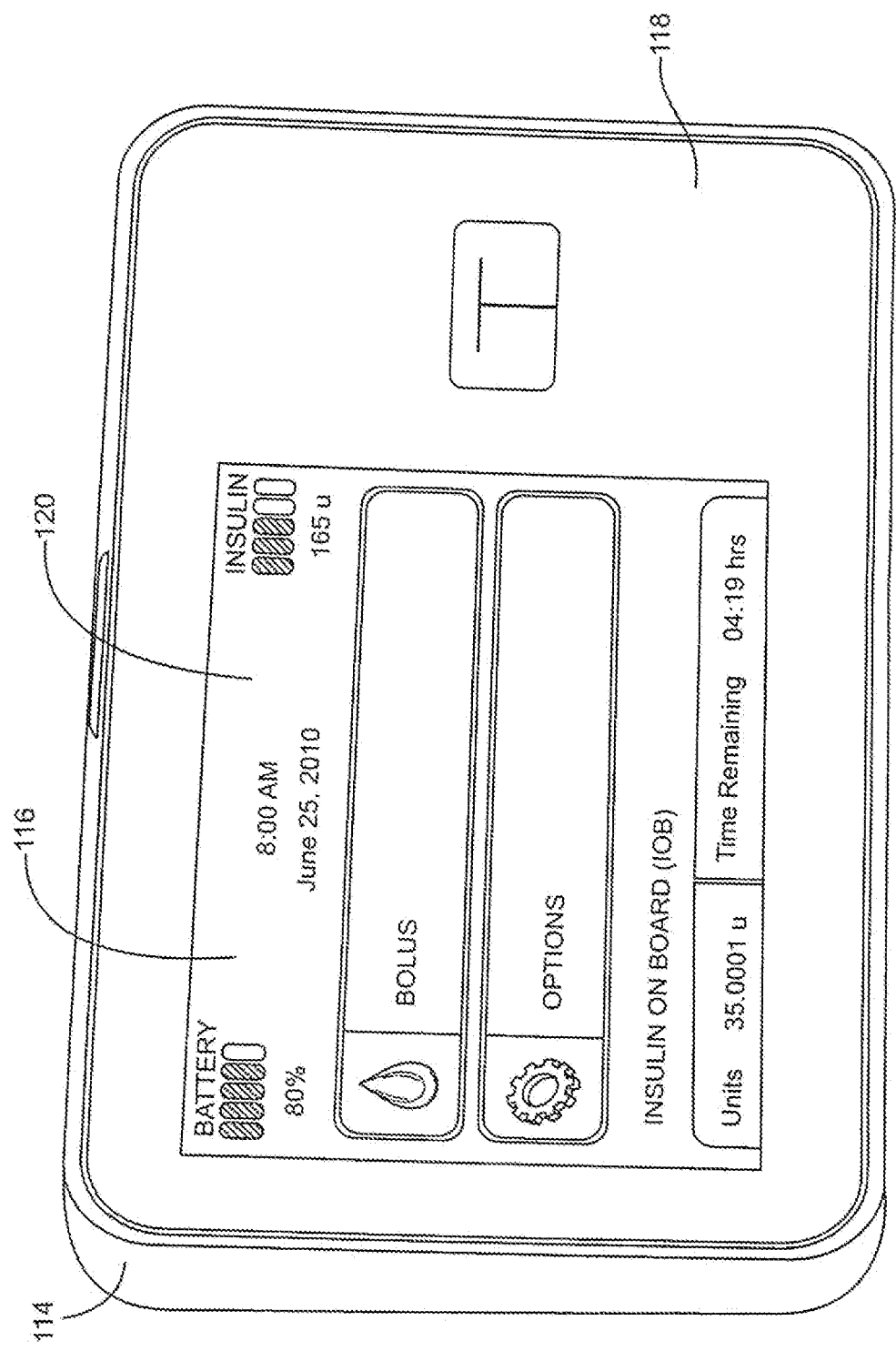
FIG. 1A is a front view in perspective of an embodiment of an infusion pump system.
Figure 1B:
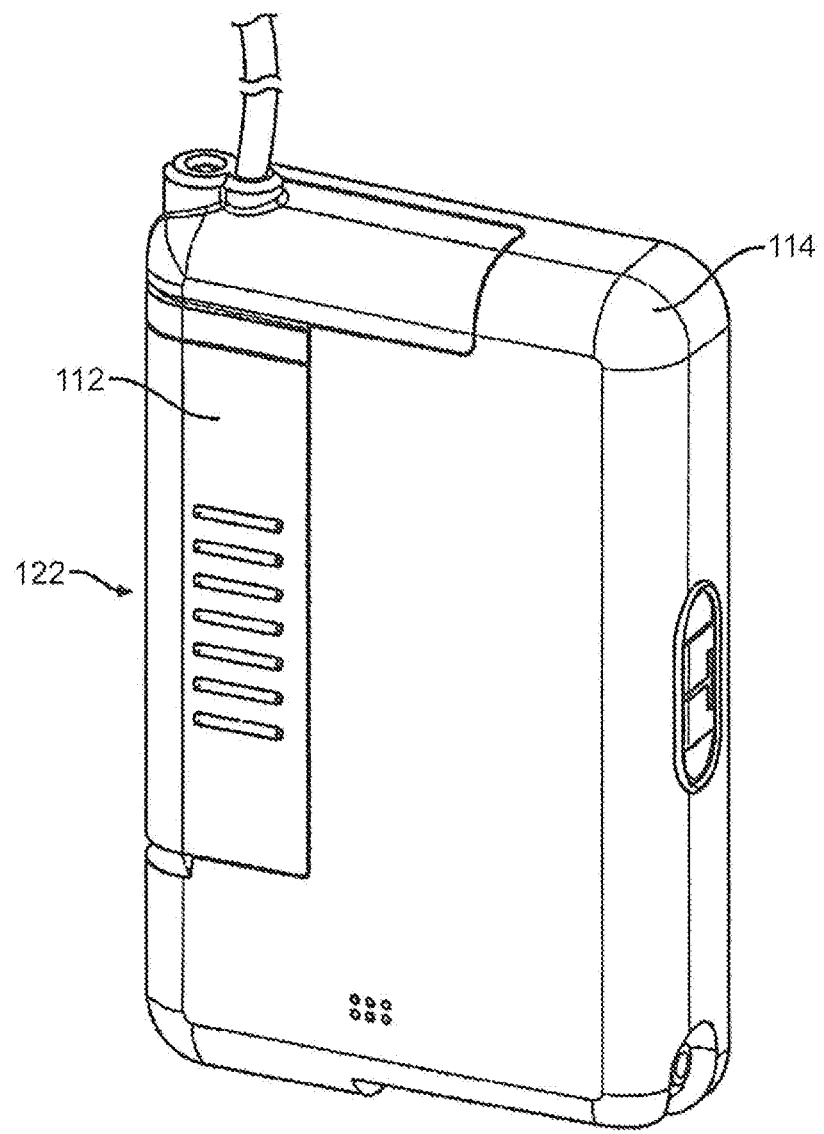
FIG. 1B is a rear view of an infusion cartridge coupled to the infusion pump device of FIG. 1A.

FIGS. 1A-1D shows an embodiment of an infusion pump system 110 including an infusion cartridge 112 and pump device 114. Infusion cartridge 112 can be a reversibly removable and interchangeable element that may be inserted into different pump devices. Referring to FIG. 1A, a front view of the pump device 114 is shown and includes a user friendly user interface 116 on a front surface 118 of the pump device 114. The user interface 116 includes a touch sensitive screen 120 that may be configured to display a variety of screens used for displaying data, facilitating data entry by a patient, providing visual tutorials, as well as other interface features that may be useful to a patient operating the pump device 114. FIG. 1B is a rear view of the pump device 114 and illustrates the detachable installment of the infusion cartridge 112 in a slot 122 of the pump device 114 which is configured to accept the cartridge 112.

Figure 1C:
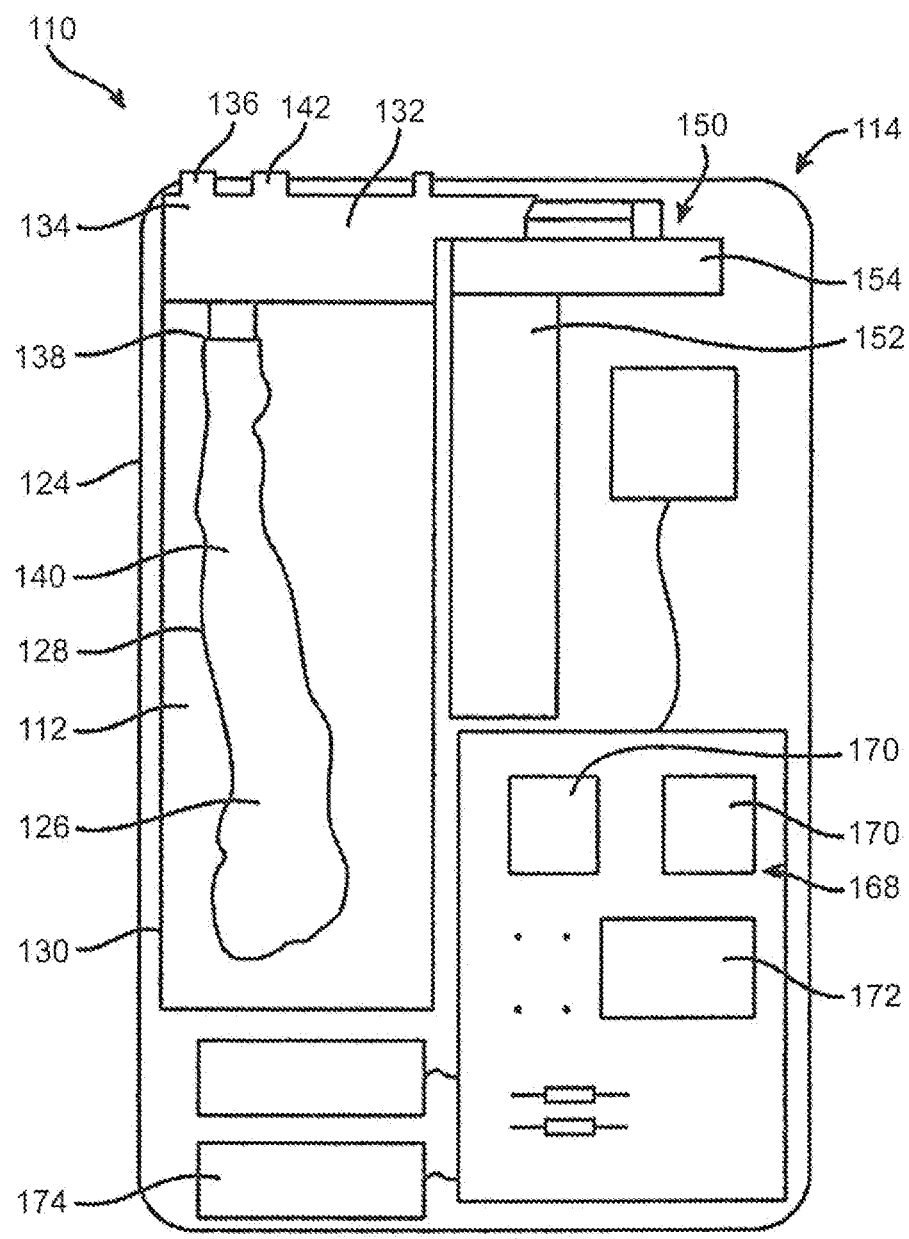
FIG. 1C is a rear schematic view of an interior of the infusion pump and cartridge embodiments of FIG. 1A.

FIG. 1C is a schematic view of an open housing 124 of the pump device 114 which shows schematically some components that may be included in embodiments of the pump device 114. The cartridge 112 may include a fluid interface configured to receive a fluid such as collapsible reservoir 126. The collapsible reservoir 126 may be formed from a flexible material or membrane 128 that is disposed about an interior volume of the reservoir 126. The cartridge 112 also includes a substantially rigid container 130 sealed around the flexible material of the collapsible reservoir 126. A disposable delivery mechanism 132 is disposed within the disposable cartridge 112 and may have a fill port 134 with a re-sealable septum 136 sealed over the fill port 134, a reservoir inlet port 138 in fluid communication with an interior volume 140 of the collapsible reservoir 126, a fluid dispense port 142 in fluid communication with a bore 144 of the delivery mechanism 132, a vent inlet port 146 and a vent outlet port 148 both in fluid communication with the bore 144. The collapsible reservoir 126 may have a bag-like structure with flexible walls that can collapse and expand depending upon the amount of material in the volume of the reservoir. The interior volume of the reservoir may be in fluid isolation from the remaining interior volume of the rigid container 130.

The cartridge 112 may be releasably and operatively secured to a housing 124 of the pump device 114. The housing 124 may be configured to house a drive mechanism 150 including a motor 152 and gear box 154 disposed in the housing 124 and detachably coupled to a spool member 156 of the delivery mechanism 132. At least one pressure sensor 158 may be disposed in a volume 160 between an outside surface 162 of the flexible material or membrane 128 of the collapsible reservoir 126 and an inside surface 164 of the substantially rigid shell or case 130. The graphic user interface 116 may be operatively coupled to a controller 168, which may include at least one processor 170, a memory device 172 and connective circuitry or other data conduits that couple the data generating or data managing components of the device. A power storage cell in the form of a battery 174 that may be rechargeable may also be disposed within the housing 124. Data generating or managing components of the device may include the processor(s) 170, the memory device 172, sensors 158, including any pressure or temperature sensors, the GUI 166 and the like.

Figure 1D:
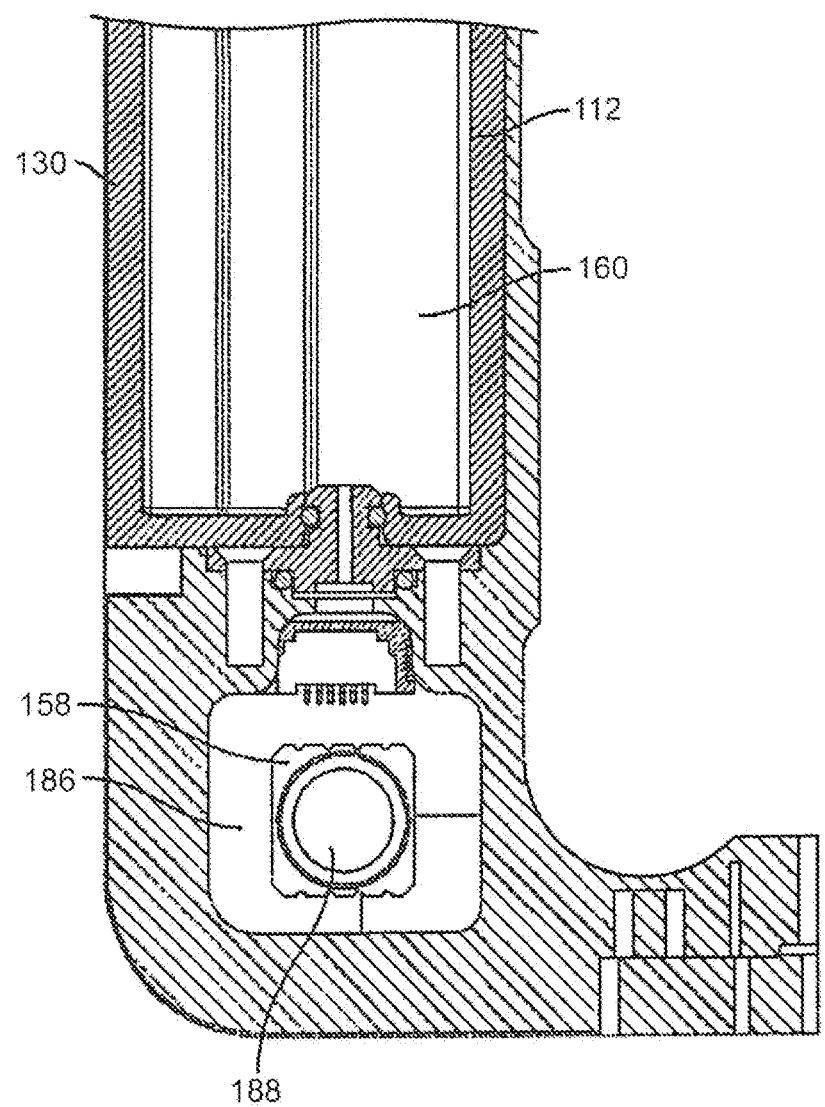
FIG. 1D illustrates a section view of a portion of the infusion cartridge and pump device of FIG. 1A.

The pressure inside the infusion cartridge 112, and particularly the vented volume 160 of the infusion cartridge 112, may be measured by a pressure sensor 158 disposed in the infusion cartridge 112 or in the pump device 114 in a volume, such as pocket 186 as shown in FIG. 1D.

Pocket 186 is an interior volume disposed within the pump device 114 and in fluid communication with an interior volume of the fluid cartridge 112. The pocket 186 is in sealed relation with the interior volume 160 of the cartridge. As such, a pressure sensor 158 disposed within the volume of the pocket 186 will read the pressure of the volume 160 in the cartridge, but can remain with the pump device 114 after disposal of the disposable cartridge 112. This configuration lowers the cost of the cartridge while providing the means of pressure measurement within the cartridge 112. In some embodiments, data from the pressure sensor 158 may be used to provide a measurement of how much insulin or other medicament is being delivered by the first pump device 114. Alternatively, the pressure sensor 158 can be disposed within the cartridge directly in the vented volume 160.

The pump device 114 can also include a thermistor or other temperature sensor 188 including an optical or infrared sensor that measures the temperature of the insulin or other medicament within the reservoir 126 upon coupling the infusion cartridge 112 with the pump device 114. Taking the temperature of the air may be important in measuring how much insulin or other medicament is in the fluid reservoir. In some embodiments, the thermistor or other temperature sensor 188 is positioned in the pocket 186 such that it can measure the temperature of the air in the pocket 186 as shown in FIG. 1D. As noted above, the pocket 186 may also include a pressure sensor 158 coupled to the controller 168 for measuring pressure within the pocket 186 and volume 160. Because the air in the pocket 186 is in fluid communication with the residual air within the chamber 160, the temperature and pressure of the air in the infusion cartridge 112 surrounding the fluid reservoir 126 may be equal or approximately equal to the temperature and pressure of the air in contact with the temperature sensor 188 and pressure sensor 158. In turn, the temperature sensor 188 may provide a relatively accurate measurement of the temperature of the insulin or other medicament within the reservoir 126.

Referring to FIGS. 2-7, an embodiment of the delivery mechanism 132 is shown in a fluid delivery cycle sequence wherein fluid from the interior volume of the reservoir 126 is drawn into the bore 220 of the delivery mechanism 132 and dispensed from the dispense outlet port 142.

Referring again to FIG. 2, a portion of the fluid reservoir cartridge 112 including a delivery mechanism 132 is shown in section as well as a portion of a drive mechanism 150 of an infusion pump. The disposable fluid cartridge 112 includes the delivery mechanism 132 which has a delivery mechanism body 236 and a bore 220 disposed in the delivery mechanism body 236. The bore 220, which may have a substantially round transverse cross section, includes a distal end 238, a proximal end 240 disposed towards the drive mechanism 150 of the infusion pump 114, an interior volume 242, a reservoir inlet port 138, a fluid dispense port 142, a vent inlet port 146 and a vent outlet port 148. The spool 156, which may also have a substantially round transverse cross section, is slidingly disposed within the bore 220 and forms a collapsible first volume 244 and a vent second volume 246 between the bore 220 and an outside surface 266 of the spool 156.

The collapsible first volume 244 of the delivery mechanism 132 may be positionable to overlap the reservoir inlet port 138 independent of an overlap of the fluid dispense port 142. The collapsible first volume 244 may be formed between a first seal 248 around the spool 156, a second seal 250 around the spool, an outer surface of the spool body between the first and second seal 250 and an interior surface 252 of the bore 220 between the first and second seal 248 and 250. The first and second seals 248 and 250 are axially moveable relative to each other so as to increase a volume of the collapsible volume 244 when the first and second seals 248 and 250 are moved away from each other and decrease the collapsible volume 244 when the seals 248 and 250 are moved closer together.

The second seal 250 is disposed on a main section 254 of the spool 156 of the delivery mechanism 132 and moves in conjunction with movement of the rest of the spool. A proximal end 196 of the spool 156 is coupled to a ball portion 194 of a drive shaft 190 of the drive mechanism 150 of the pump device 114. The drive mechanism 150 includes a rack and pinion 192 mechanism actuated by an electric motor 152 through a gear box 154. As such, the second seal 250 moves or translates axially in step with axial translation of the spool 156 and drive shaft 190. The first seal 248, however, is disposed on a distal section 258 of the spool 156 which is axially displaceable with respect to the main section 254 of the spool 156. The distal section of the spool 156 is coupled to the main section of the spool by an axial extension 260 that is mechanically captured by a cavity 261 in the main section 254 of the spool 156. This configuration allows a predetermined amount of relative free axial movement between the distal section 258 of the spool and the nominal main section 254 of the spool 156.

For some embodiments, a volume of a "bucket" of fluid dispensed by a complete and full dispense cycle of the spool 156 may be approximately equal to the cross section area of the bore 220 multiplied by the length of displacement of the captured axial extension of the spool 156 for the distal section 258. The complete bucket of fluid may also be dispensed in smaller sub-volumes in increments as small as a resolution of the drive mechanism 150 allows. For some embodiments, a dispense volume or bucket defined by the complete collapsible volume 244 of the delivery mechanism 132 may be divided into about 10 to about 100 sub-volumes to be delivered or dispensed. In some cases, the maximum axial displacement between the distal section and main section of the spool may be about 0.01 inch to about 0.04 inch, more specifically, about 0.018 inch, to about 0.022 inch.

Figure 2:
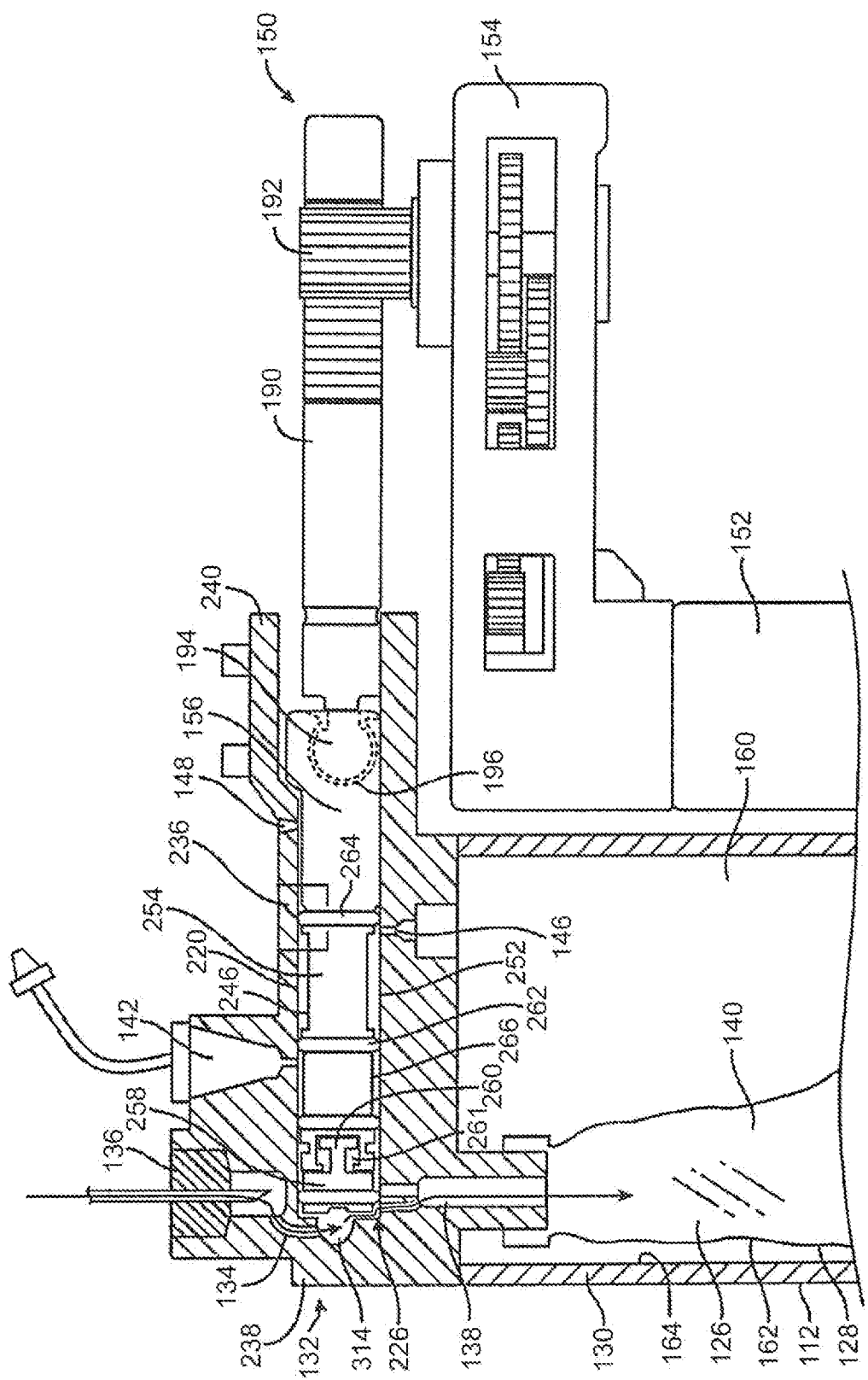
FIG. 2 is a section view of a delivery mechanism of an infusion pump with the spool of the delivery mechanism positioned at a distal hard stop for filling of the expandable reservoir according to an embodiment of the present invention.
Figure 3:
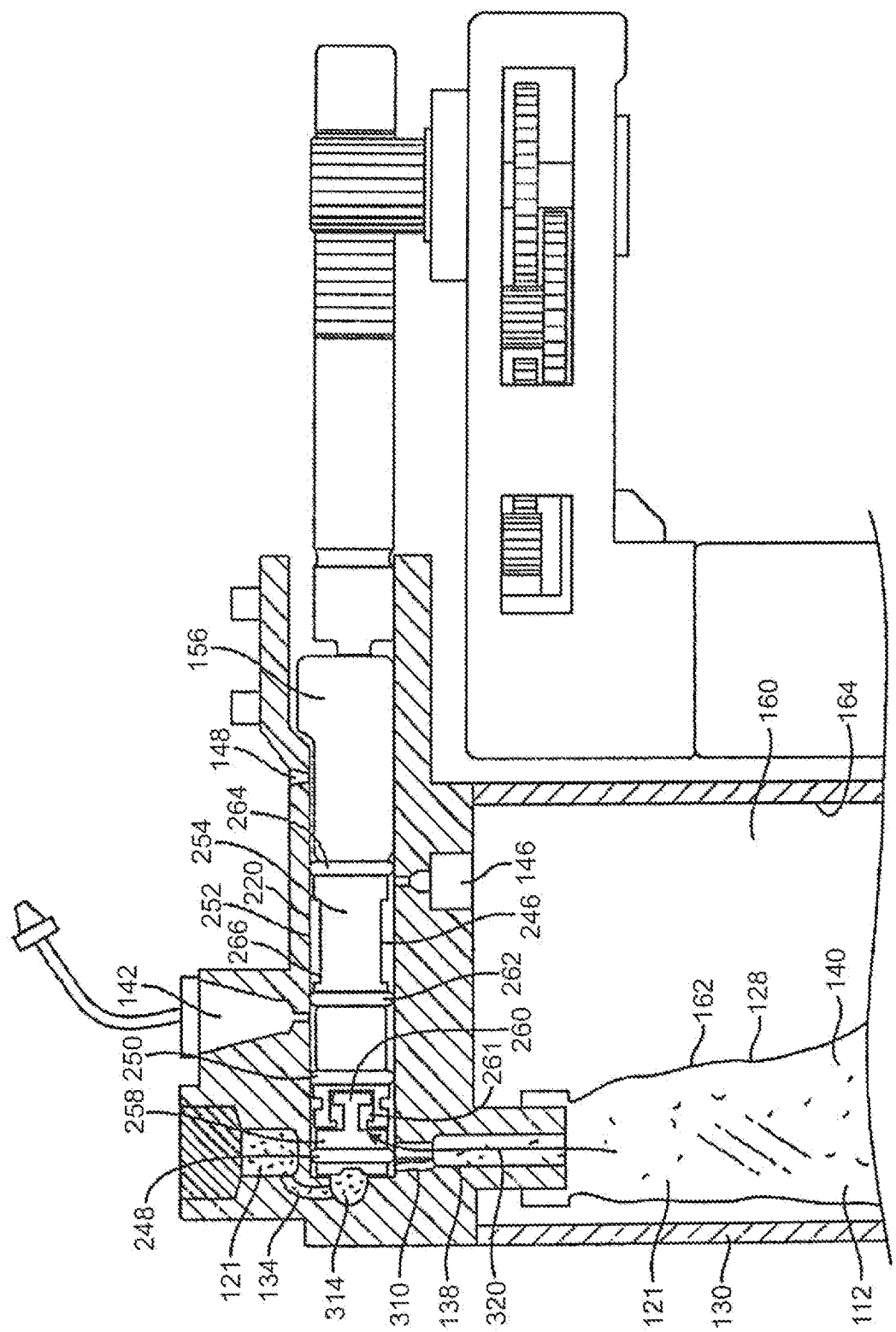
FIG. 3 is a section view of the delivery mechanism embodiment of FIG. 2 with the spool of the delivery mechanism positioned for filling of a collapsible volume of the spool.

In use, once the reservoir cartridge 112 of the infusion pump system 110 has been installed or otherwise snapped into place in the slot 122 of the pump device 114, the interior volume 140 of the collapsible reservoir 126 may then be filled with a desired fluid 121 for dispensing. In order to fill the reservoir 126, the spool 156 may be translated by the drive mechanism 150 to a hard stop position 226 as shown in FIG. 2. In the hard stop position 226 the first seal 248 is disposed proximally of a relief port 310, the relief port 310 being disposed in fluid communication between a distal end 238 of the bore 220 and the reservoir volume 140. In the hard stop position, the first seal 248 is also disposed distally of the reservoir inlet port 138. In the hard stop position, a distal end 316 of the spool 156 is contacting the distal end 238 of the bore 220 or a shoulder portion 312 of the distal end 238 of the bore 220 to prevent any further distal displacement of the spool 156.

A reservoir fill port 134 is disposed on a top portion of the bore 220 substantially opposite the bore 220 of the reservoir inlet port 138. With the spool 156 and seals 248, 250, 262 and 264 thereof so positioned, a patient may then obtain an amount of a desired fluid to be dispensed. In some cases, if the desired fluid to be dispensed is insulin or other suitable medicament, the patient 127 typically stores the insulin in a refrigerated glass container. The insulin is then accessed with a hypodermic needle 222 of a syringe device and drawn into an interior volume of the syringe (not shown). The tip of the hypodermic needle 222 of the syringe may then be pushed through a septum membrane 136 that seals the reservoir fill port 134 as shown and fluid manually dispensed from the interior volume of the syringe, through the hypodermic needle 222, through a bubble trap volume 314 in the bore 220 of the delivery mechanism 132 and into the interior volume 140 of the collapsible reservoir 126 of the cartridge 112 as shown by the arrow 318 in FIG. 2.

As discussed above with regard to other embodiments of the delivery mechanism 132, the vented volume 160 of the cartridge 112 disposed between an outside surface 162 of the flexible membrane 128 of the collapsible reservoir 126 and an inside surface 164 of the rigid shell 130 may include or be in operative communication with a pressure sensor 158. The pressure sensor 158 may be used to monitor the pressure within the vented volume 160 during the filling of the collapsible reservoir 126. The controller 168 of the pump system 114 may be programmed with information regarding the fixed volume of the rigid shell 130 of the cartridge 112 and configured to calculate the volume of fluid loaded into the collapsible reservoir 126 based on the pressure rise within the rigid shell 130 upon filling of the collapsible reservoir 126. The data regarding the volume of fluid loaded into the collapsible reservoir 126 may be stored and used to calculate and display data later in the use cycle such as fluid remaining in the collapsible reservoir 126 and the like.

Once the collapsible reservoir 126 contains a desired amount of a fluid 121 to be dispensed, a dispense cycle may be initiated by driving the spool 156 with the drive mechanism 150 based on commands from a controller 168 of the pump device to a position with the collapsible first volume 244 in communication with the reservoir inlet port 138. The hard stop position shown in FIG. 2 is such a position. If the spool 156 has been driven to this hard stop position 226 in a distal direction from previous proximal position, the friction generated between the first seal 248 of the spool 156 and the inside surface 252 of the bore 220 will have collapsed the collapsible volume 244 of the delivery mechanism 132 with the first seal 248 and second seal 250 in a least axially separated state. In this state, the collapsible volume 244 has a minimum volume. Such a state of the delivery mechanism 132 is shown in FIG. 2. Once in this pre-fill position, the spool 156 may then be driven so as to axially separate the first and second seals 248 and 250 (and the main section 254 of the spool 156 and distal section 258 of the spool 156) of the collapsible first volume 244 and draw fluid into the first volume 244 through the reservoir inlet port 138 from the reservoir 126 as shown by the arrow 320 in FIG. 3. As the fluid 121 is drawn into the collapsible volume 244, the pressure within the vented volume 160 decreases. As previously discussed, this drop in pressure may be used in accordance with the ideal gas law to determine the amount of material taken from the collapsible reservoir 126. An unexpected reading based on the magnitude of the translation of the main section 254 of the spool 156 may also be used to detect a failure of a portion of the delivery mechanism 132 in some cases.

Figure 4:
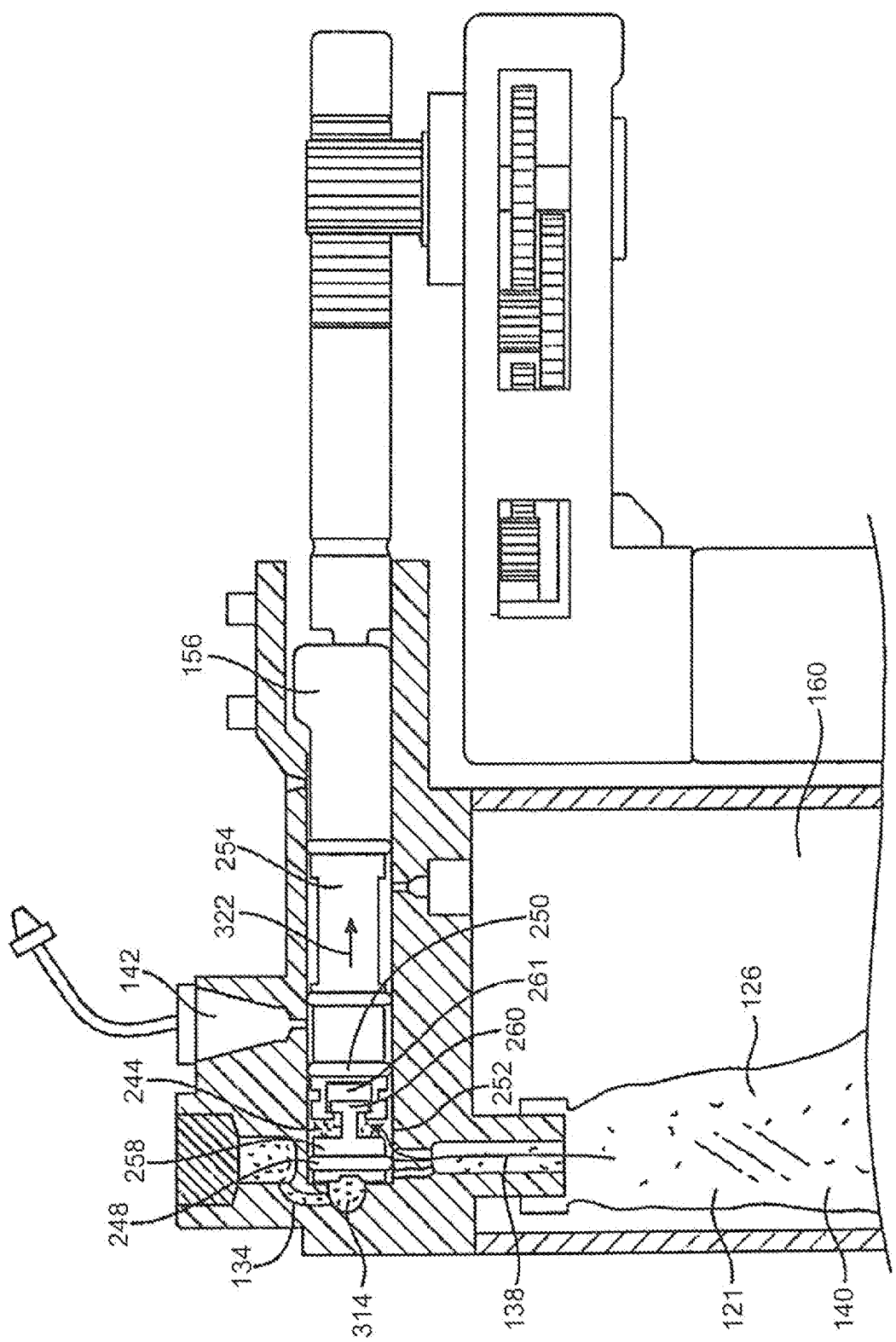
FIG. 4 is a section view of the delivery mechanism embodiment of FIG. 2 with the spool of the delivery mechanism positioned after filling of the collapsible volume of the spool.
Figure 5:
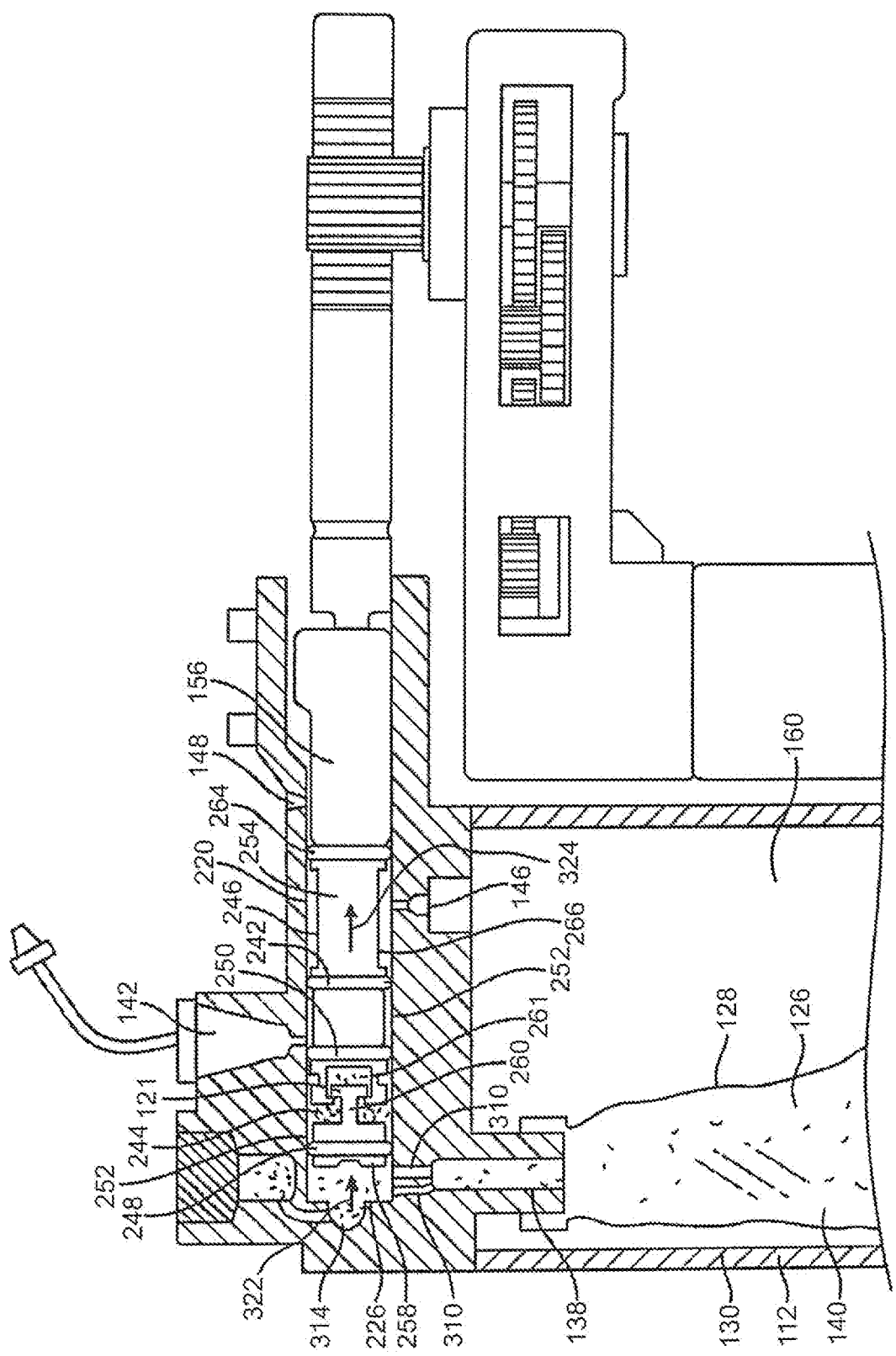
FIG. 5 shows the spool of FIG. 2 with the collapsible volume of the device full of fluid being displaced proximally towards the dispense port of the device.

The collapsible volume 244 of the delivery mechanism 132 may be completely filled by proximally retracting the main section 254 and second seal 250 of the spool 156 relative to the first seal 248 and distal section 258 of the spool 156 as shown by arrow 322 on spool 156 in FIG. 4. Once filled, the spool 156 may then be driven in a proximal direction as shown in FIG. 5 wherein there are two seals 248 and 250 disposed in the bore 220 between the reservoir inlet port 138 and relief port 310 and the dispense port 142. As shown by arrow 323 and arrow 324 in FIG. 5, both the main section 254 and distal section 258 of the spool 156 are proximally retracted together. The captured axial extension of the distal section 258 by the main section 254 pulls the distal section along without axial displacement between the main section 254 and distal section 258 of the spool 156 The dispense port may be in fluid communication with a subcutaneous portion of a patient's body. The delivery mechanism 132 always includes at least one seal 248 or 250 disposed in the bore 220 between the reservoir volume 140 and material 121 disposed therein and the dispense port 142 in order to prevent a free flow condition wherein the material 121 in the reservoir 126 is in uninterrupted communication with the patient's body.

Figure 6:
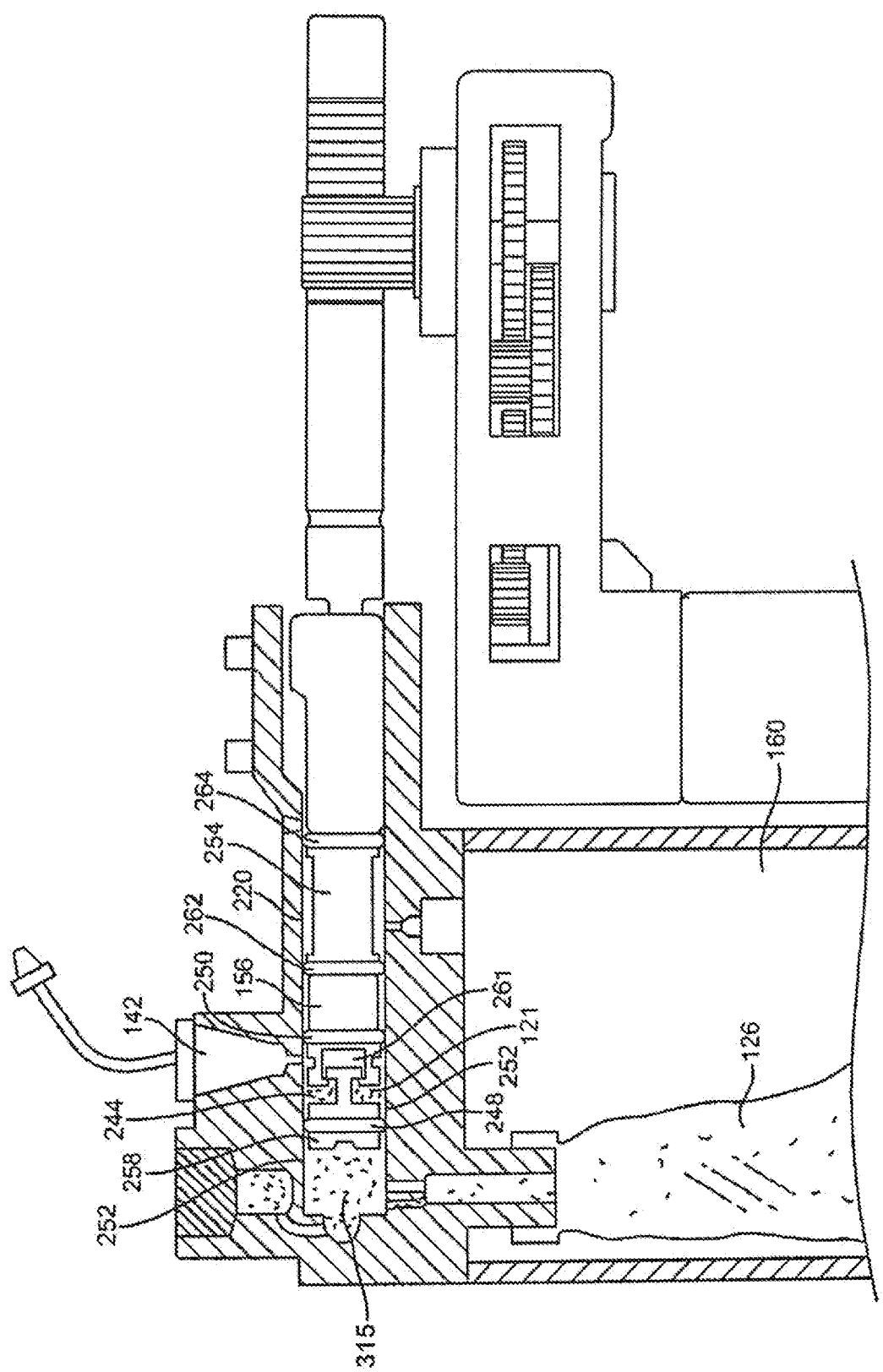
FIG. 6 is a section view of the delivery mechanism embodiment of FIG. 2 with the spool of the delivery mechanism positioned prior to delivery of fluid into the dispense port from the collapsible volume of the spool.
Figure 7:
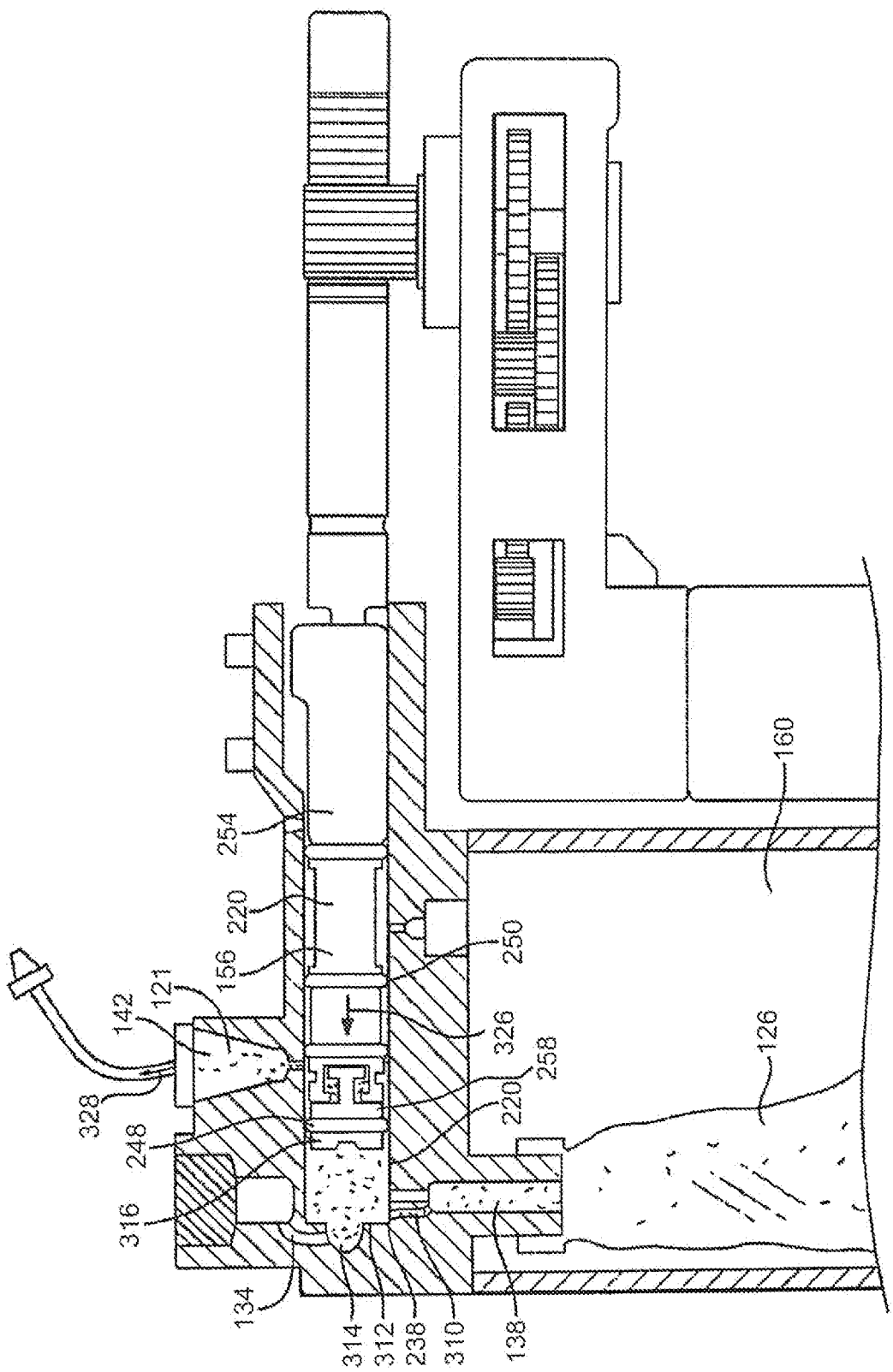
FIG. 7 is a section view of the delivery mechanism embodiment of FIG. 2 with the spool of the delivery mechanism positioned after delivery of fluid from the collapsible volume of the spool into the dispense port.

Once filled, the spool 156 and filled collapsible volume 244 may be proximally displaced with the drive mechanism 150 to a position with the collapsible first volume 244 in communication with the fluid dispense port 142 of the bore 220 as shown in FIG. 6. Once the spool 156 is positioned as shown in FIG. 6, the main section of the spool 156 may then be axially driven in a distal direction by the drive mechanism 150 with the distal section 258 of the spool remaining stationary or substantially stationary. This axial distal movement of the main section 254 as indicated by arrow 326 on the spool 156 shown in FIG. 7, serves to at least partially collapse the collapsible first volume 244. Collapsing the first volume 244 of the delivery mechanism 132 dispenses fluid from the collapsible first volume 244 through the fluid dispense port 142 as shown by the arrow 328 in FIG. 7. Once all fluid from the collapsible first volume 244 is dispensed in this manner, additional cycles as described above can be completed to provide additional insulin to the patient. Further details on the operation and configuration of such an infusion pump can be found in U.S. Pat. No. 8,287,495, which is hereby incorporated by reference herein in its entirety.

Figure 8:
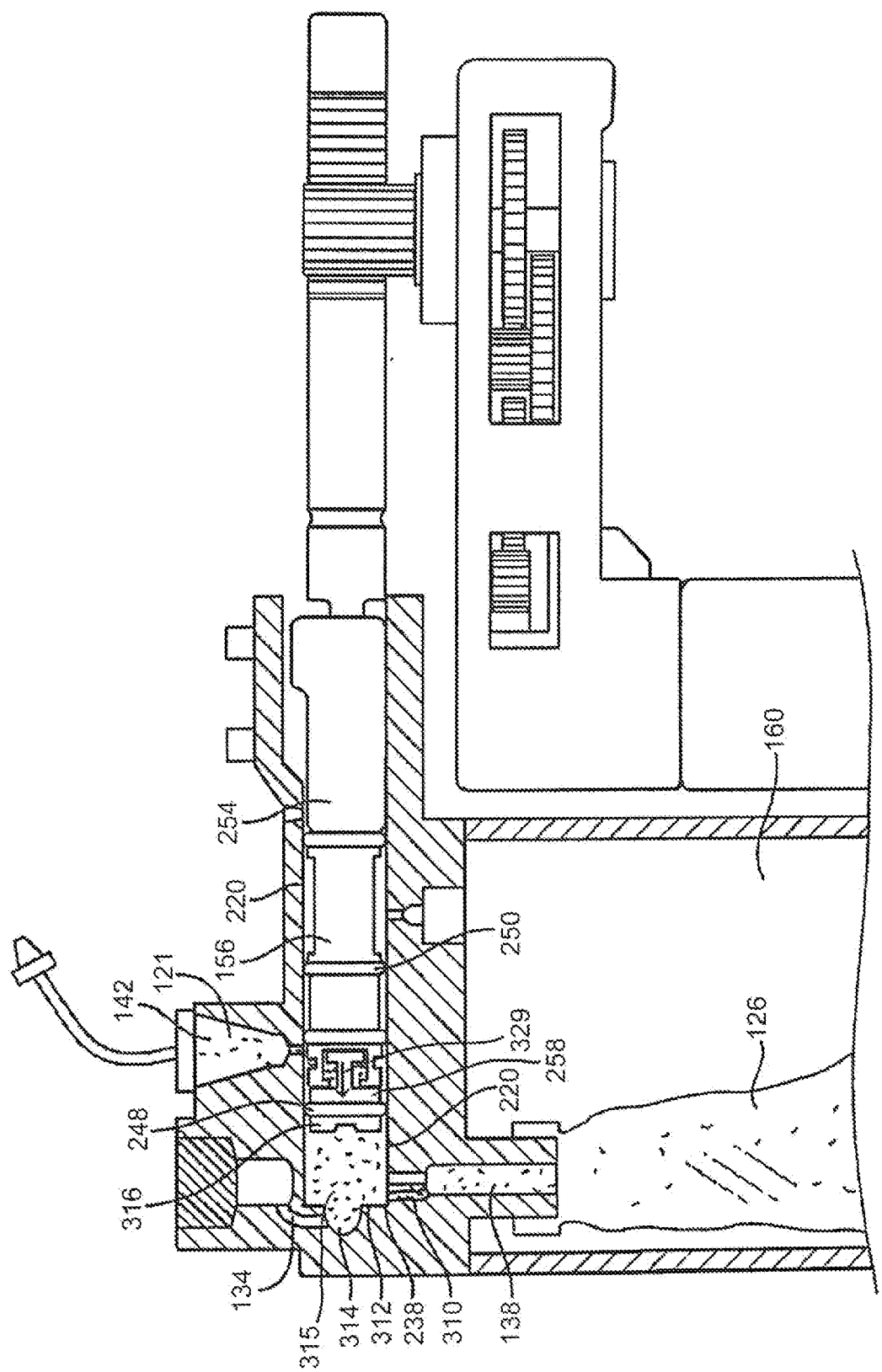
FIG. 8 is a graph depicting a rise in blood glucose over time that occurs after an ingestion of food, particularly an ingestion of carbohydrates.

FIG. 8 is a graph schematically depicting a rise in blood glucose over time that occurs after ingestion of food; particularly, ingestion of carbohydrates. The rise in blood glucose occurs in people suffering from diabetes because of insufficient insulin production or production of insulin that is ineffectively used. This at least partially uncontrolled rise in blood glucose is a contributor to the sequelae of diabetes that include microvascular changes in the eyes and elsewhere in the body. Complications of diabetes include retinopathy, nephropathy and neuropathy as well as cardiovascular disease.

According to the invention, current insulin pump therapies in which a bolus of insulin is typically delivered abruptly and quickly, thus creating a rapid rise in insulin level, are modified to provide more effective blood sugar modulation—particularly in the case of the use of rapid-acting insulins and complementary drug therapies.

Figure 9A:
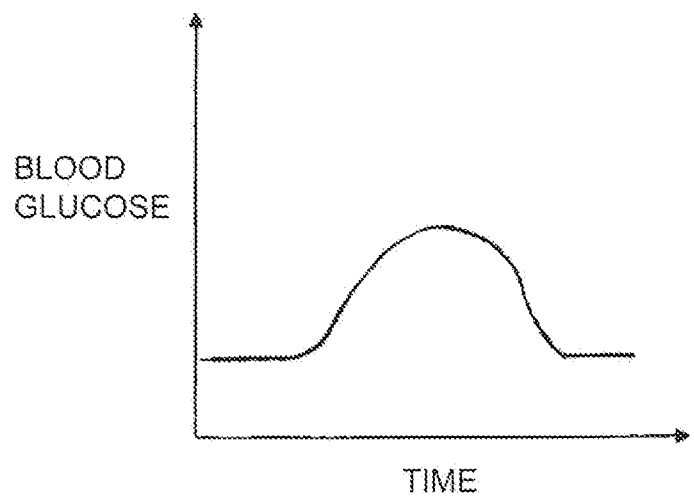
FIGS. 9A-9B are graphs depicting a rise in blood glucose over time that is reduced in amplitude and lengthened in time occurs after an ingestion of carbohydrates and use of pramlintide or a similar agent.
Figure 9B:
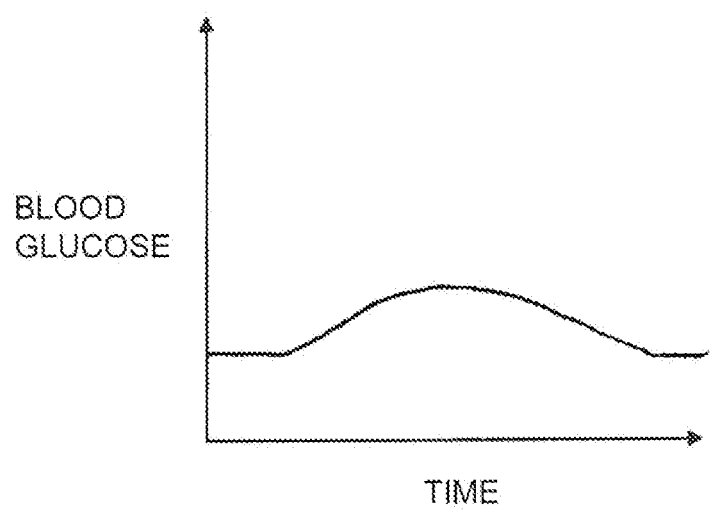

FIG. 9 is a graph schematically depicting a more gradual rise in blood glucose over time, with the blood glucose level having a reduced amplitude and a lengthened time course as compared to FIG. 8. This sort of postprandial rise in blood sugar occurs, for example, when gastric emptying is slowed. This occurs, for example, when a medication such as pramlintide or a GLP-1 agonist is used. Because gastric emptying is slowed, the absorption of food is slowed and the rise in blood sugar is in turn more gradual and has a lower peak amplitude over time.

Figure 10:
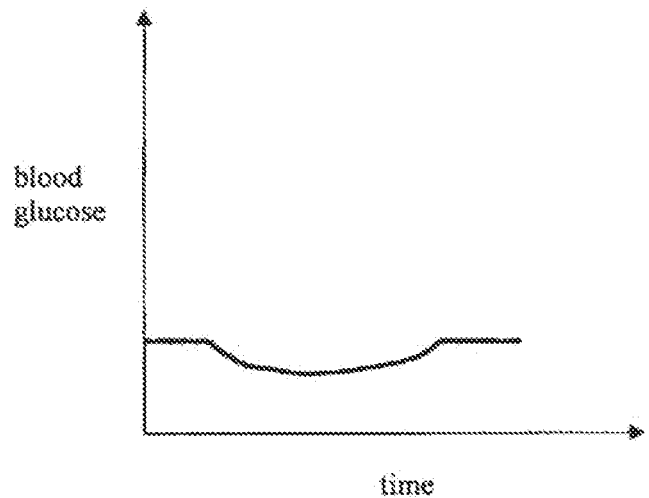
FIG. 10 is a graph depicting an undesirable postprandial drop in blood glucose over time that occurs after an ingestion of carbohydrates in the presence of other circumstances such as infusion of an ultra-rapid acting insulin, use of pramlintide or similar agents.

FIG. 10 is a graph schematically depicting an undesirable postprandial drop in blood glucose over time that can occur under certain circumstances that are addressed by embodiments of this invention. This atypical drop in blood glucose can occur, e.g., after an ingestion of carbohydrates in the presence of other circumstances.

Circumstances that can cause a postprandial drop in blood glucose include infusion of ultra-rapid-acting insulin, where the action of the insulin is faster than the expected rise in blood sugar. Thus, insulin is metabolized more quickly than are carbohydrates, and an undesirable drop in blood glucose may occur. Having an undesirable drop in blood glucose can lead to a circumstance where insufficient blood glucose is available for nutrition and can lead to problems. Such problems can include in extreme cases, insulin shock which can cause serious harm or in rare cases even death. Neuroglycopenia is another concern that can arise when blood glucose level drops to a level below that needed for normal physiological function. Neuroglycopenia occurs when the brain does not receive sufficient glucose to support brain metabolism and to function properly. Neuroglycopenia can present with a wide variety of neurological symptoms including confusion, ataxia, fatigue, anxiety, moodiness and depression.

Another circumstance that can cause an undesirable postprandial drop in blood glucose is the use of pramlintide or a GLP-1 agonist in combination with insulin therapy. If the rise in blood glucose has been modified as in FIG. 9, a conventionally-used bolus of insulin may cause an undesirable quick metabolism of blood glucose, thus resulting in the aforementioned postprandial drop in blood glucose.

Thus, with the benefit of the invention and the embodiments discussed herein, it is expected that blood glucose can be maintained at a relatively constant level without an undesirable postprandial drop in blood glucose.

Figure 11:
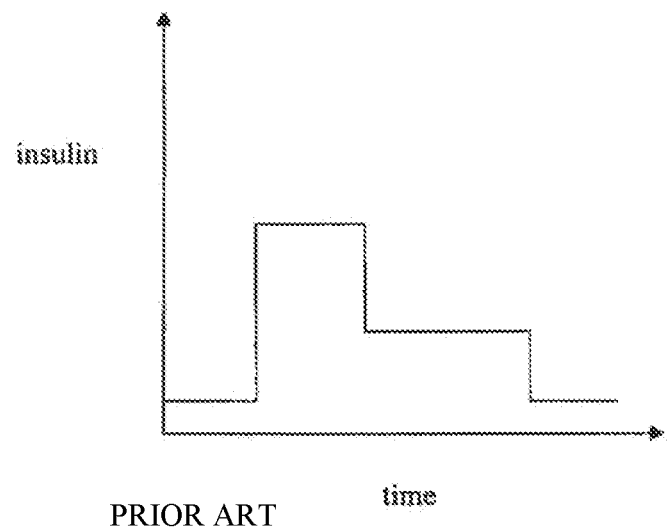
FIG. 11 is a graph depicting a typical prior art insulin bolus delivery with a bolus extension.

FIG. 11 is a graph schematically depicting a typical prior art insulin bolus delivery profile, with a bolus extension, as a function of time. As can be seen, a bolus of insulin may be delivered quickly, causing a relatively large quantity of insulin to be infused and to be present in the blood stream relatively rapidly in anticipation of a blood glucose rise that would otherwise occur with ingestion of carbohydrates. The bolus extension is intended to cover the metabolism of insulin over time after the initial rise in blood glucose that would already occur.

Figure 12:
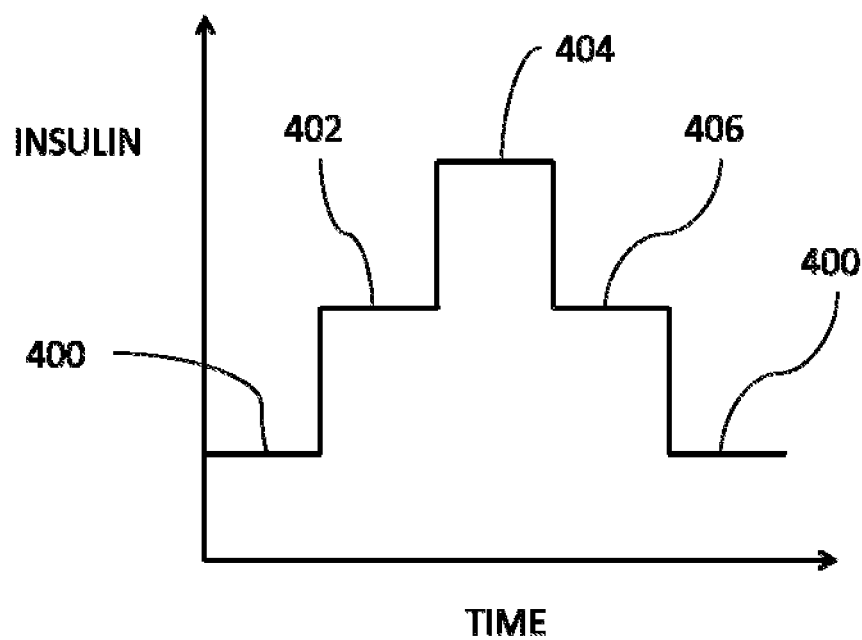
FIG. 12 is a graph depicting an alternative insulin delivery protocol according to an example embodiment of the invention.

Referring now to FIG. 12, an alternative insulin delivery protocol according to an example embodiment of the invention is depicted in schematic form as a function of time. According to this example embodiment of the invention, insulin is delivered at a basal level 400, followed by a first small bolus 402, followed by a larger bolus 404 and then a second small bolus 406. After second small bolus 406, insulin delivery returns to the basal level 400. As can be seen, this delivery of insulin more closely aligns with the expected rise in blood glucose as depicted in FIG. 8. Accordingly, an insulin delivery protocol according to this embodiment of the invention is well suited to maintain blood glucose at a more constant level.

Figure 13:
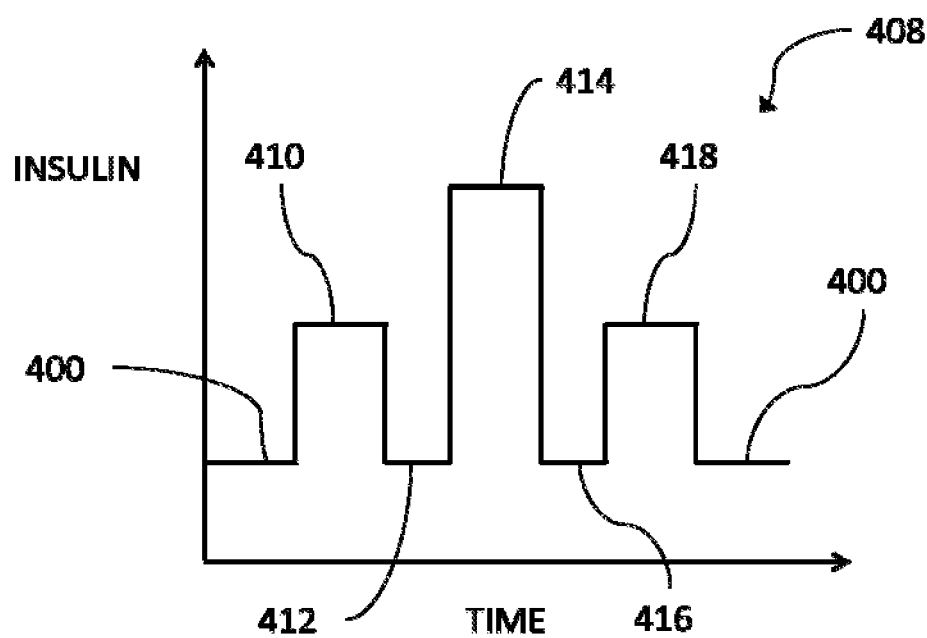
FIG. 13 is a graph depicting another alternative insulin delivery protocol according to an example embodiment of the invention.

Referring now to FIG. 13, another insulin delivery protocol 408 is depicted in schematic form as a function of time. According to this embodiment of the invention, insulin is maintained at a basal level 400 followed by first small bolus 410. This is then followed by first rest period 412 in which insulin delivery returns to a basal level 400. This is then followed by a larger bolus 414 which in turn is followed by second rest period 416 during which insulin delivery returns to a basal level 400. Finally, a second small bolus 418 is delivered followed by a return to basal level 400. Again, it is expected in the circumstance of a blood sugar rise similar to that depicted in FIG. 8, a more constant blood glucose level would be maintained within this delivery protocol than prior art delivery protocols. The relative heights of the different insulin delivery levels in FIGS. 12 and 13 are for example only. Those of ordinary skill in the art can adjust the size of the bolus deliveries in order to accommodate an expected blood glucose rise.

Figure 14:
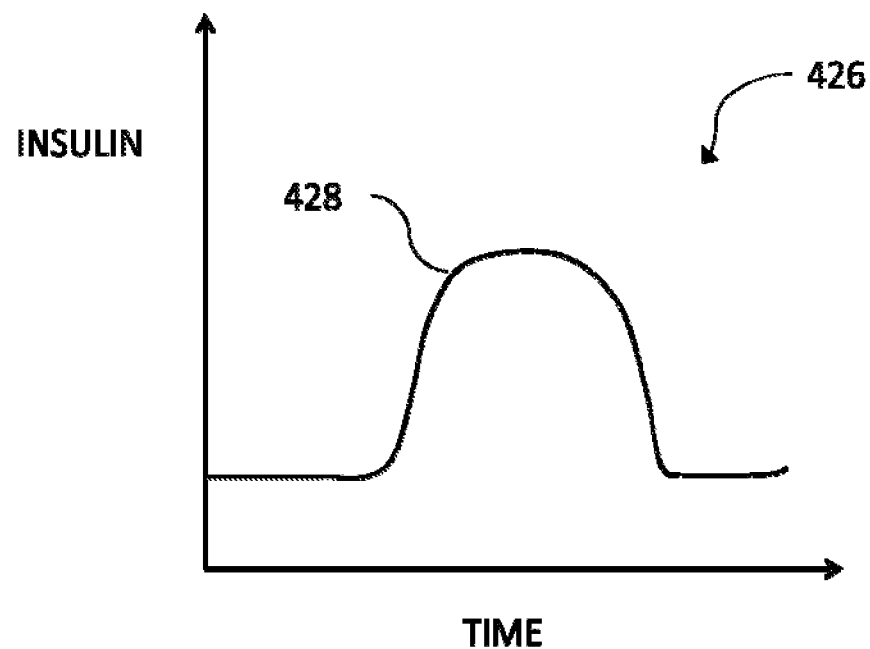
FIG. 14 is a graph depicting another alternative insulin delivery protocol having a Gaussian curve-like structure according to an example embodiment of the invention.

Referring now to FIG. 14, another insulin delivery protocol 426 is depicted in schematic form as a function of time. As can be seen by examination of FIG. 14, in insulin delivery protocol 426 a Gaussian-shaped insulin bolus 428 is delivered. In other words, the delivery of insulin approximates a Gaussian curve. It should be understood that the insulin delivery in this protocol 426 does not necessarily have to be in the form of an exact Gaussian curve as mathematically defined; rather, it approximates a Gaussian curve in that there is a gradual rise in insulin delivery to a peak followed by a gradual decline in insulin delivery as time progresses. This curve is expected to approximate the expected rise in blood glucose over time as depicted in FIG. 8 and thus is expected to provide a relatively constant level of blood glucose over the time of insulin delivery. Gaussian insulin bolus 428 may also have a lower peak in order to accommodate an expected blood glucose rise similar to that depicted in FIG. 9.

Figure 15:
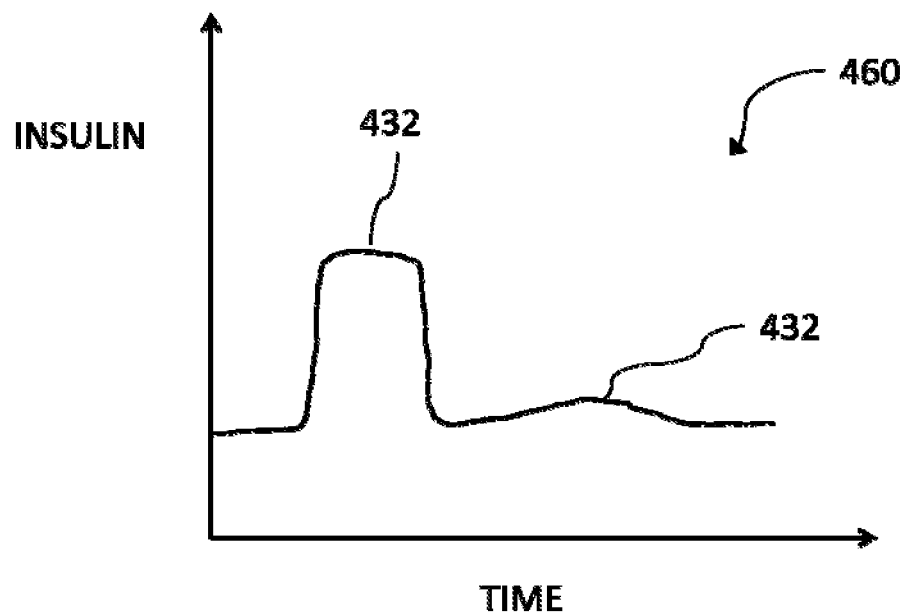
FIG. 15 is a graph depicting another alternative insulin delivery protocol including an initial bolus followed by a Gaussian curve-like extension according to an example embodiment of the invention.

FIG. 15 depicts another insulin delivery protocol 460 in schematic form as a function of time, including insulin bolus 432 and Gaussian extension 434. According to this embodiment of the invention, an initial insulin bolus 432 is delivered followed by an extension that is not constant in insulin delivery but that gradually rises and falls over time, approximating a Gaussian curve. As discussed above, this is not intended to describe a curve that is precisely mathematically Gaussian in structure but a curve that gradually rises and then gradually falls. The curve may be, but need not be, generally symmetrical.

Figure 16:
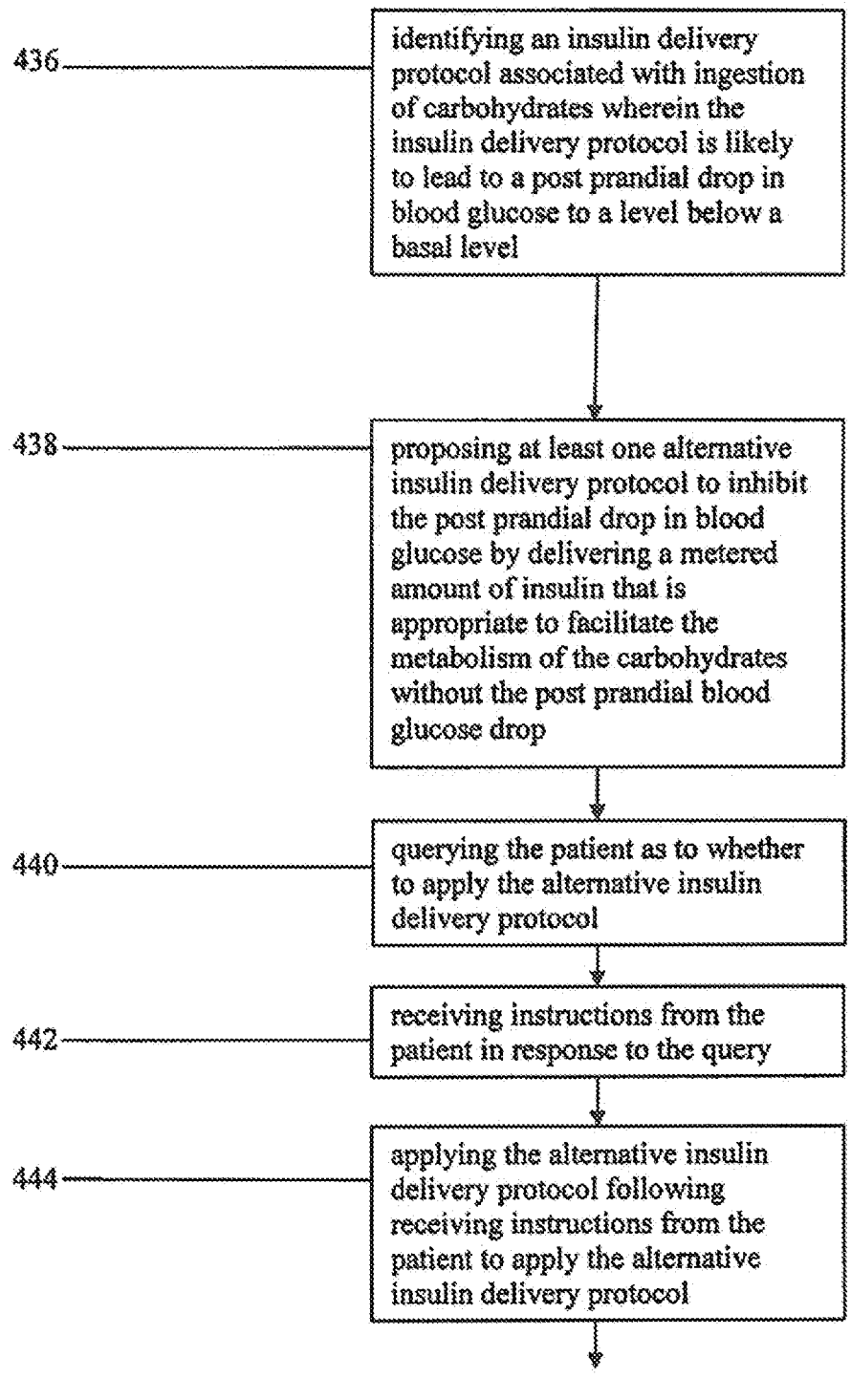
FIG. 16 is a flowchart depicting methods according to an example embodiment of the invention.
Figure 16:
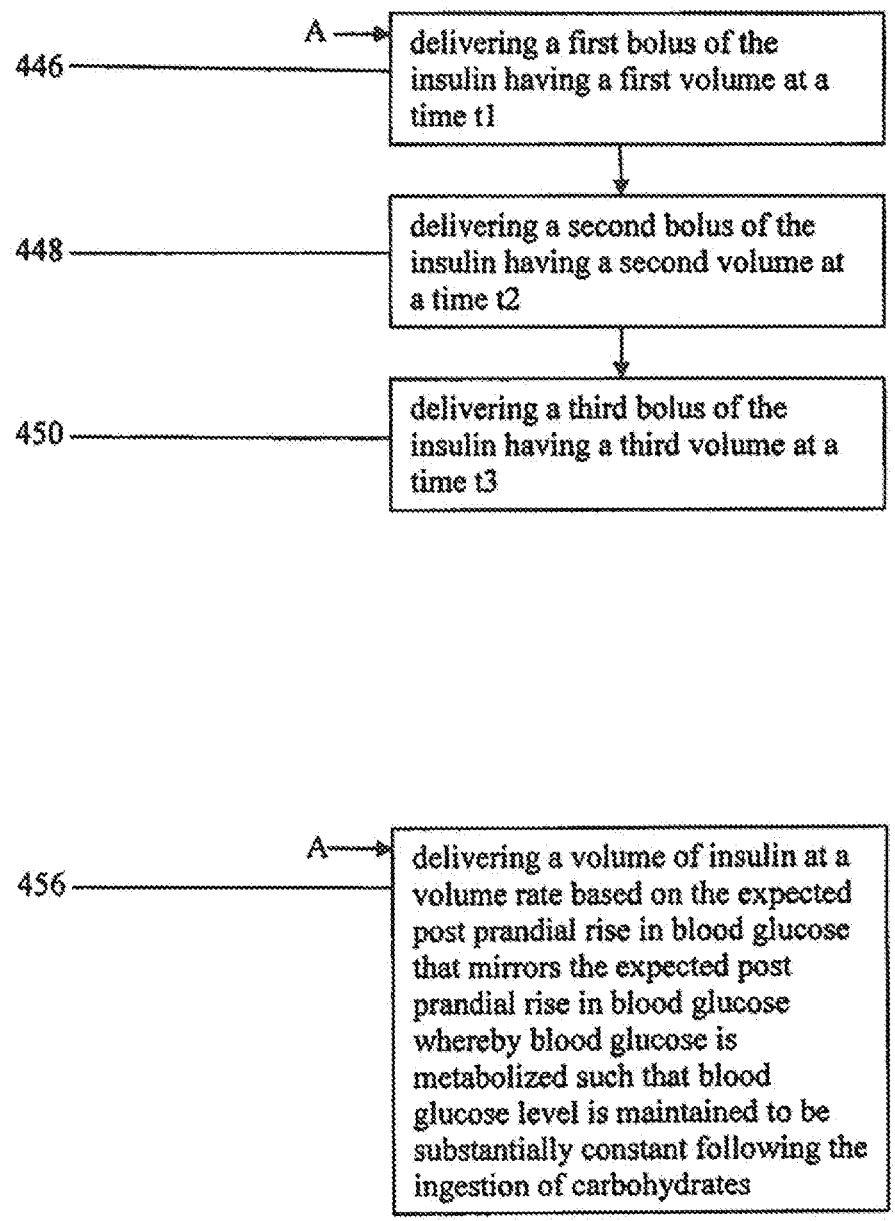
Figure 16:
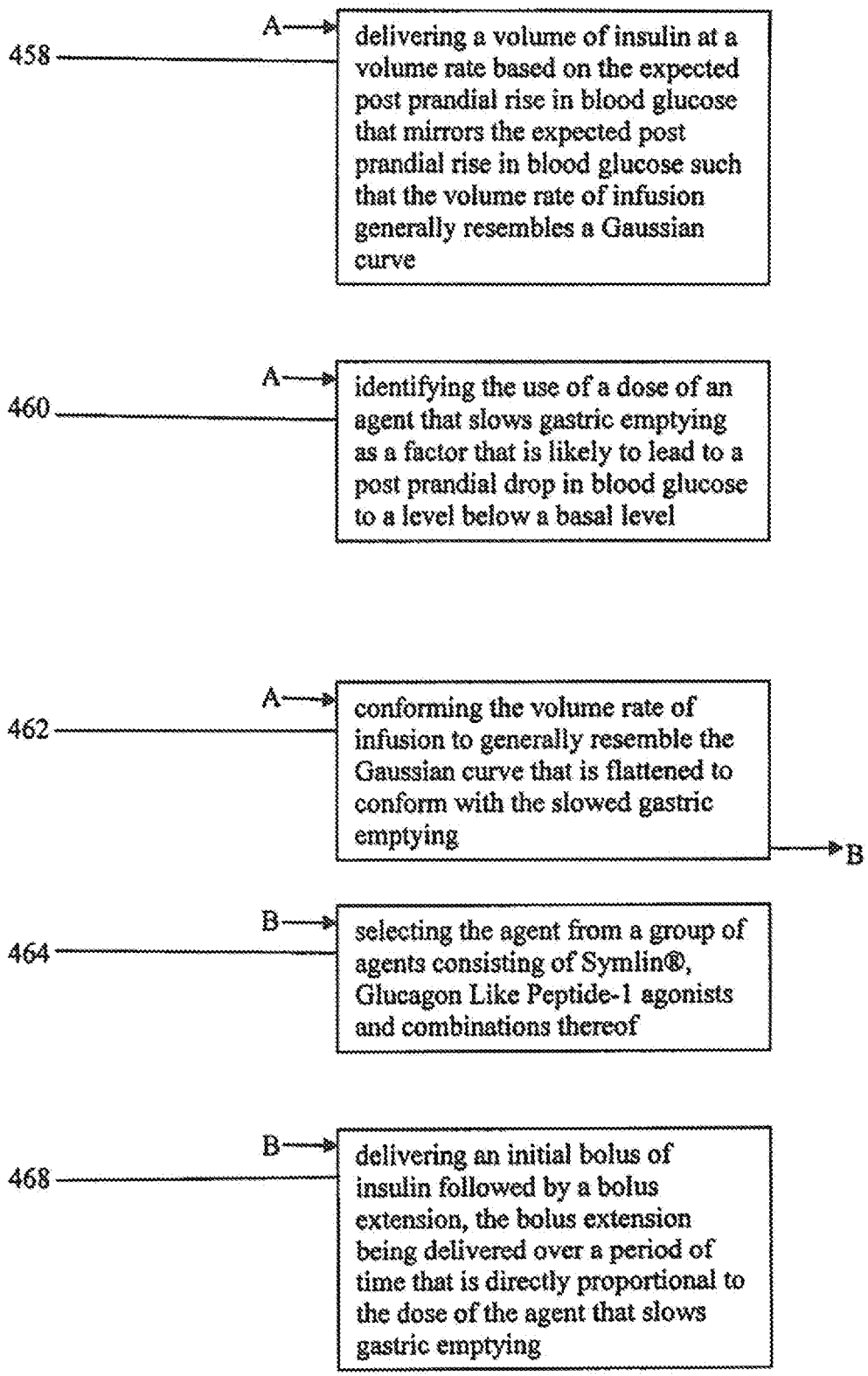
Figure 16:
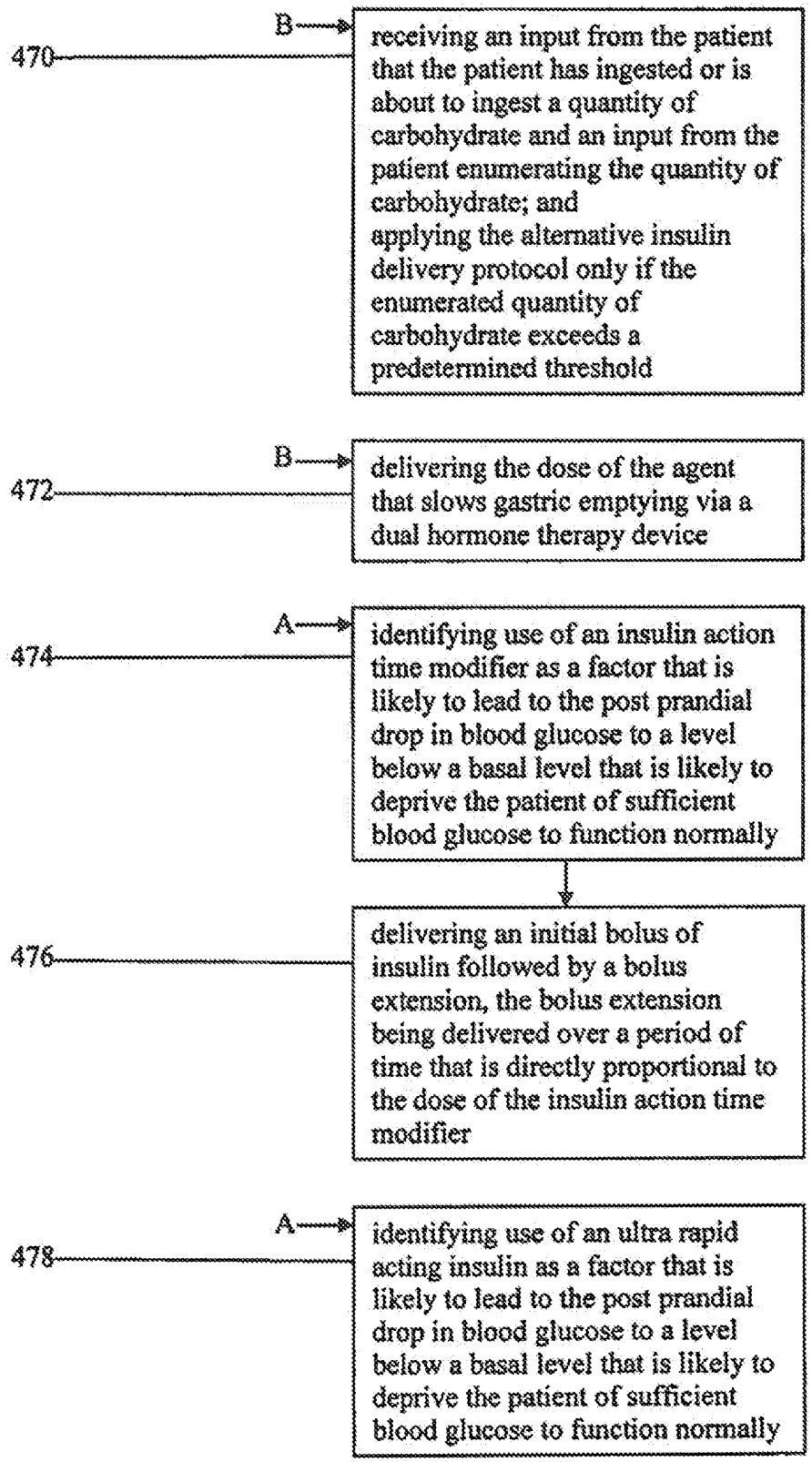
Figure 16:
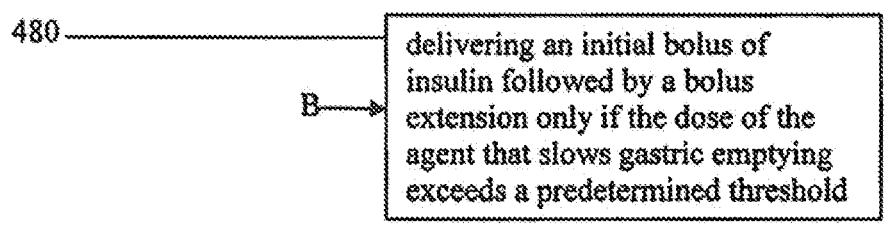

Referring now to FIG. 16, a flow chart depicting a method according to the invention is depicted. This method may be implemented in the operation of an insulin pump that includes a controller such as that described herein.

A method according to the invention for infusing liquid medicaments including insulin, via an insulin pump having at least one reservoir containing the liquid medicaments includes identifying an insulin delivery protocol associated with ingestion of carbohydrates wherein the insulin delivery protocol is likely to lead to a postprandial drop in blood glucose to a level below a basal level that is likely to deprive a patient of sufficient blood glucose to function normally 436. The method may further include proposing at least one alternative insulin delivery protocol to inhibit the postprandial drop in blood glucose by delivering a metered amount of insulin that is appropriate to facilitate the metabolism of the carbohydrates without the postprandial blood glucose drop 438. The method may further include querying the patient as to whether to apply the alternative insulin delivery protocol 440 and receiving instructions from the patient in response to the query 442 and applying the alternative insulin delivery protocol following receiving instructions from the patient to apply the alternative insulin delivery protocol 444.

According to another embodiment of the invention, the invention may include delivering a first bolus of the liquid medicament having a first volume at a time t1 446, delivering a second bolus of the liquid medicament having a second volume at a time t2 448 and delivering a third bolus of the liquid medicament having a third volume at a time t3 440.

According to another embodiment of the invention, the invention may further include delivering an initial bolus followed by a bolus extension, the bolus extension rising and falling in volume in a cyclical wave fashion over a period of time 452.

According to another example embodiment of the invention, the method may include delivering insulin over an extended period of time during which the volume of insulin delivered rises and falls in a cyclical wave fashion over a period of time and then declines to a basal level 454.

According to another example embodiment of the invention, the method further includes delivering a volume of insulin at a volume rate based on the expected postprandial rise in blood glucose that mirrors the expected postprandial rise in blood glucose whereby blood glucose is metabolized such that blood glucose level is maintained to be substantially constant following the ingestion of carbohydrates 456.

According to another example embodiment of the invention, the method further includes delivering a volume of insulin at a volume rate based on the expected postprandial rise in blood glucose that mirrors the expected postprandial rise in blood glucose such that the volume rate of infusion generally resembles a Gaussian curve 458.

According to another embodiment of the invention, the method may include identifying the use of a dose of an agent that slows gastric emptying as a factor that is likely to lead to a postprandial drop in blood glucose to a level below a basal level that is likely to deprive a patent of sufficient blood glucose to function normally 460.

According to another embodiment of the invention, the method may include conforming the volume rate of infusion to generally resemble the Gaussian curve that is flattened to conform with the slowed gastric emptying 462.

According to another example embodiment, the method may include selecting the agent from a group of agents consisting of pramlintide, GLP-1 agonists and combinations thereof 464.

According to another embodiment of the invention, the method may include delivering an initial bolus of insulin followed by a bolus extension, the bolus extension being delivered over a period of time that is directly proportional to the dose of the agent that slows gastric emptying 468.

According to another embodiment of the invention, the method may include receiving an input from the patient that the patient has ingested or is about to ingest a quantity of carbohydrate and an input from the patient enumerating the quantity of carbohydrate; and applying the alternative insulin delivery protocol only if the enumerated quantity of carbohydrate exceeds a predetermined threshold 470.

According to another embodiment of the invention, the method further includes delivering the dose of the agent that slows gastric emptying via a dual hormone therapy device 472.

According to another embodiment of the invention, the method may include identifying use of an insulin action time modifier as a factor that is likely to lead to the postprandial drop in blood glucose to a level below a basal level that is likely to deprive the patient of sufficient blood glucose to function normally 474.

This method may further include delivering an initial bolus of insulin followed by a bolus extension, the bolus extension being delivered over a period of time that is directly proportional to the dose of the insulin action time modifier 476.

According to another embodiment, the method may further include identifying use of an ultra-rapid acting insulin as a factor that is likely to lead to the postprandial drop in blood glucose to a level below a basal level that is likely to deprive the patient of sufficient blood glucose to function normally 478.

According to another embodiment, the method may further include delivering an initial bolus of insulin followed by a bolus extension only if the dose of the agent that slows gastric emptying exceeds a predetermined threshold 480.

Rapid changes in blood glucose level can cause patients with diabetes to feel uncomfortable or emotionally out of balance in ways that patients find hard to describe. This can occur when an excessively large insulin bolus is delivered or if the patient engages in exercise with an excess of insulin in his system. With increasing speed of insulin action it may be desirable to extend even correction boluses to reduce the rate of change of blood sugar level. Thus, according to another embodiment, the invention includes an alternative insulin delivery protocol wherein a correction bolus is delivered that includes a correction bolus extension to moderate the rate at which blood glucose change occurs. According to another embodiment, the invention includes utilizing an alternative insulin delivery protocol that maintains the rate of change of blood glucose below a preselected level.

The present invention may be embodied in other specific forms without departing from the spirit of the essential attributes thereof; therefore, the illustrated embodiments should be considered in all respects as illustrative and not restrictive, reference being made to the appended claims rather than to the foregoing description to indicate the scope of the invention.

The invention claimed is:

1. An ambulatory infusion pump, comprising:
   a reservoir configured to contain a medicament for treatment of diabetes;
   a pumping mechanism configured to deliver the medicament in the reservoir to a user;
   a memory configured to store one or more medicament delivery protocols for delivery of the medicament to the user; and
   a processor configured to:
   determine a type of medicament contained in the reservoir;
   modify a medicament delivery protocol of the one or more medicament delivery protocols to an alternate medicament delivery protocol of the one or more medicament delivery protocols based on the type of medicament contained in the reservoir; and
   cause the pumping mechanism to deliver the type of medicament contained in the reservoir to the user according to the alternate medicament delivery protocol.

2. The ambulatory infusion pump of claim 1, wherein the alternate medicament delivery protocol includes delivery of a modified volume of the type of medicament contained in the reservoir relative to a volume defined in the medicament delivery protocol.

3. The ambulatory infusion pump of claim 2, wherein the modified volume is determined based on differences between how the type of medicament contained in the reservoir and another type of medicament affect blood glucose.

4. The ambulatory infusion pump of claim 2, wherein one or more ratios are stored in the memory and the modified volume is determined based on at least one of the one or more ratios.

5. The ambulatory infusion pump of claim 1, wherein the processor modifies the medicament delivery protocol when the type of medicament contained in the reservoir will cause an undesirable drop in blood glucose if delivered according to the medicament delivery protocol.

6. The ambulatory infusion pump of claim 1, wherein the medicament delivery protocol relates to delivery of a bolus of medicament.

7. The ambulatory infusion pump of claim 1, wherein the medicament delivery protocol relates to basal medicament delivery.

8. The ambulatory infusion pump of claim 1, wherein the processor is configured to automatically modify the medicament delivery protocol to the alternate medicament delivery protocol.

9. An ambulatory infusion pump system, comprising:
an ambulatory infusion pump including a reservoir configured to contain a medicament and a pumping mechanism configured to deliver medicament in the reservoir to a user;
a memory configured to store one or more medicament delivery protocols for delivery of the medicament to the user;
and
a processor configured to:
determine a type of medicament contained in the reservoir;
modify a medicament delivery protocol of the one or more medicament delivery protocols to an alternate medicament delivery protocol of the one or more medicament delivery protocols based on the type of medicament contained in the reservoir; and
cause the pumping mechanism to deliver the type of medicament contained in the reservoir to the user according to the alternate medicament delivery protocol.

10. The ambulatory infusion pump of claim 9, wherein the alternate medicament delivery protocol includes delivery of a modified volume of the type of medicament contained in the reservoir relative to a volume defined in the medicament delivery protocol.

11. The ambulatory infusion pump of claim 10, wherein the modified volume is determined based on differences between how the type of medicament contained in the reservoir and another type of medicament affect blood glucose.

12. The ambulatory infusion pump of claim 10, wherein one or more ratios are stored in the memory and the modified volume is determined based on at least one of the one or more ratios.

13. The ambulatory infusion pump of claim 9, wherein the medicament delivery protocol is modified to the alternative medicament delivery protocol when the type of medicament contained in the reservoir will cause an undesirable drop in blood glucose if delivered according to the medicament delivery protocol.

14. The ambulatory infusion pump of claim 9, wherein the medicament delivery protocol relates to delivery of a bolus of medicament.

15. The ambulatory infusion pump of claim 9, wherein the medicament delivery protocol relates to basal medicament delivery.

16. The ambulatory infusion pump of claim 9, wherein the processor is configured to automatically modify the medicament delivery protocol to the alternate medicament delivery protocol.

* * * * *